US006825217B2

(12) United States Patent
Carliss et al.

(10) Patent No.: US 6,825,217 B2
(45) Date of Patent: Nov. 30, 2004

(54) CARBINOLS FOR THE TREATMENT OF NEUROPATHIC DYSFUNCTION

(75) Inventors: Richard Carliss, Westchester, PA (US); David A. H. Lee, Chadds Ford, PA (US)

(73) Assignee: Endo Pharmaceuticals, Inc., PA (US)

( * ) Notice: Subject to any disclaimer, the term of this patent is extended or adjusted under 35 U.S.C. 154(b) by 0 days.

(21) Appl. No.: 10/272,375

(22) Filed: Oct. 16, 2002

(65) Prior Publication Data

US 2003/0162811 A1 Aug. 28, 2003

Related U.S. Application Data

(60) Provisional application No. 60/329,869, filed on Oct. 16, 2001.

(51) Int. Cl.$^7$ .............................................. A61K 31/445
(52) U.S. Cl. ........................ 514/326; 514/212; 514/318; 514/422; 540/596; 540/597; 540/602; 540/609; 546/193; 546/212; 546/240; 548/517; 548/518; 548/527; 548/574
(58) Field of Search ................................. 514/212, 318, 514/326, 422; 540/596, 597, 602, 609; 645/193, 212, 240; 548/517, 518, 527, 574

(56) References Cited

U.S. PATENT DOCUMENTS

| | | | |
|---|---|---|---|
| 3,080,372 A | | 3/1963 | Janssen |
| 3,108,111 A | | 10/1963 | Stern et al. |
| 4,485,109 A | | 11/1984 | Ciganek |
| 4,522,811 A | | 6/1985 | Eppstein et al. |
| 5,019,650 A | | 5/1991 | Ciganek et al. |
| 5,086,063 A | * | 2/1992 | Ciganek et al. ............. 514/326 |

FOREIGN PATENT DOCUMENTS

| | | |
|---|---|---|
| CA | 2 423 860 | 3/2003 |
| WO | WO 02/28817 | 4/2002 |

OTHER PUBLICATIONS

Bannon et al. :ABT–594 a novel cholinergic channel . . . CA 129:225607 (1998).*
Buschmann et al. "Preparation of aryldimethylaminomethyl . . . " CA 136:294640 (2002).*
Tremont–Lukats et al. "Anticonveslants for neuropathic . . . " CA 135:86334 (2002).*
Wong et al. "metabolism and disposition . . . " CA 120:68(1993).*
Bannon et al. "Broad spectrum nonopioid . . . " CA 128:176098 (1998).*
Radl et al. "Synthesis and antinociceptive . . . "CA 130:352171 (1999).*
Kim, S.H. and Chung, J.M. "Sympathectomy alleviates mechanical allodynia in an experimental animal model for neuropathy in the rat" *Neurosci. Lett.* 1991, 134, 131–134.

Kupers, R. et al. "The consumption of fentanyl is increased in rats with nociceptive but not with neuropathic pain" *Pain*, 1995, 60, 137–141.

Lee, S.H. et al. "Differential action of morphine and various opioid agonists of thermal allodynia and hyperalgesia in mononeuropathic rats" *Pain*, 1994, 57, 233–240.

Marchand, Fabien et al. "Evidence for a monoamine mediated, opioid–independent, antihyperalgesic effect of venlafaxine, a non–tricyclic antidepressant, in a neurogenic pain model in rats" *Pain*, 103, 229–235.

Matthes, Hans et al. "Loss of morphine–induced analgesia, reward effect and withdrawal symptoms in mice lacking the μ–opioid–receptor gene" *Nature*, Oct. 31, 1996, 383, 819–823.

Pan, Hui–Lin et al. "Gabapentin Suppresses Ectopic Nerve Discharges and Reverses Allodynia in Neuropathic rats" *J. Pharm. Ex. Therap.* 199, 288(3), 1026–1030.

Seltzer, A. et al. "A Novel behavioral model of neuropathic pain disorders produced in rats by partial sciatic nerve injury" *Pain*, 1990, 43, 205–218.

Siegmund, Estelle et al. "A Method for Evaluating both Non–Narcotic and Narcotic Analgesics" *Proc. Exp. biol. Med.*, 1957, 95, 729–731.

Tal, Michael et al. "Dextrophan relieves neuropathic heat–evoked hyperalgesia in the rat" *Neuroscience Letters*, 1993, 151, 107–110.

Tremont–Lukat et al. "Anticonvulsants for neuropathic pain syndrome: mechanisms of action and place in therapy" *Drugs*, Nov. 2000, 60 (5), 1029–1052.

Bannon et al. "ABT–594, a novel cholinergic channel modulator, is efficacious in nerve ligation and diabetic neuropathy models of neuropathic pain" *Brain Research*, Aug. 10, 1998, 801 (1–2), 158–163.

Bennett, Gary "7 Neuropathic Pain: An Overview" *Molecular Neurobiology of Pain*, Progress in Pain Research and Management, vol. 9, ed. D. Borsook, ISAP Press, Seattle, 1997.

Bennett, Gary J. et al. "A peripheral mononeuropathy in rat that produces disorders of pain sensation like those seen in man" *Pain*, 1988, 33, 87–107.

Blumberg, Harold et al. "Use of Writhing Test for Evaluating Analgesic Activity of Narcotic Antagonists" *Proc. Exp. biol. Med.*, 1965, 118, 763–766.

(List continued on next page.)

*Primary Examiner*—Celia Chang
(74) *Attorney, Agent, or Firm*—Piper Rudnick LLP

(57) ABSTRACT

Compositions and methods are provided for treating neuropathic pain or neuropathic dysfunction that include the administration of an effective amount of a defined carbinol or a pharmaceutically acceptable salt or prodrug thereof.

58 Claims, 12 Drawing Sheets

OTHER PUBLICATIONS

Kim, S.H. and Chung, J.M. "An experimental model for peripheral neuropathy produced by segmental spinal nerve ligation in the rat" *Pain*, 1992, 50, 355–363.

Bergel F. et al., *J. Chem. Soc.*, 26, (1944).

Blumberg, et al., *Proc. Exp. Biol. Med.* 118: 763–767, 1965.

Bondesson U. et al., *Acta Pharm. Suec.*, 11, 1 (1980).

Bondesson U. et al., *Drug Metab. Dispos.*, 9, 376 (1981).

Davis, J. L.: Smith, R. L. "Painful peripheral diabetic neuropathy treated with venlafaxine HCl extended release capsules" *Diabetes Care* 199, 22(11):1909–10.

Diamond J., W. F. Bruce, and F. T. Tyson, *J. Org. Chem.*, 22, 299 (1957).

Imamoto T., Y. Sagiura, and N. Takiyama, *Tetrahedron Lett*, 25, 4233 (1984).

Iorio, M. A. et al., *Tetrahedron*, 4983 (1971).

Jacoby R. L., K. A. Nieforth, and R. E. Willete, *J. Med. Chem.*, 17,453 (1974).

Kagi, H. et al., *Helv. Chim. Acta*, 7,2489 (1949).

Kiayias, J. A.; Vlachou E. D.; Lakka–Papadodima, E. "Venlafaxine HCl in the treatment of painful peripheral diabetic neuropathy" *Diabetes Care*, 2000, 23(5):699.

Litchfield and Wilcoxon, *J. Pharmacol. Exp. Ther.* 96:99–113, 1949.

Macdonald, A. D. et al., *Brit J. Pharmacol.*, 1,4 (1946).

Morrison, A. L. et al., *J. Chem. Soc.*, 1467, (1950).

Pernia, A.; Mico, J. A.; Calderon, E.; Torres, L. M. "Venlafaxine for the treatment of neuropathic pain" *J Pain Symptom Manage*, 2000, 19(6):408–10.

Siegmund et al. *Proc. Soc. Exp. Biol. Med.* 95: 729–731, 1957.

Thompson, *Bacteriological Rev.* 11: 115–145, 1947.

\* cited by examiner

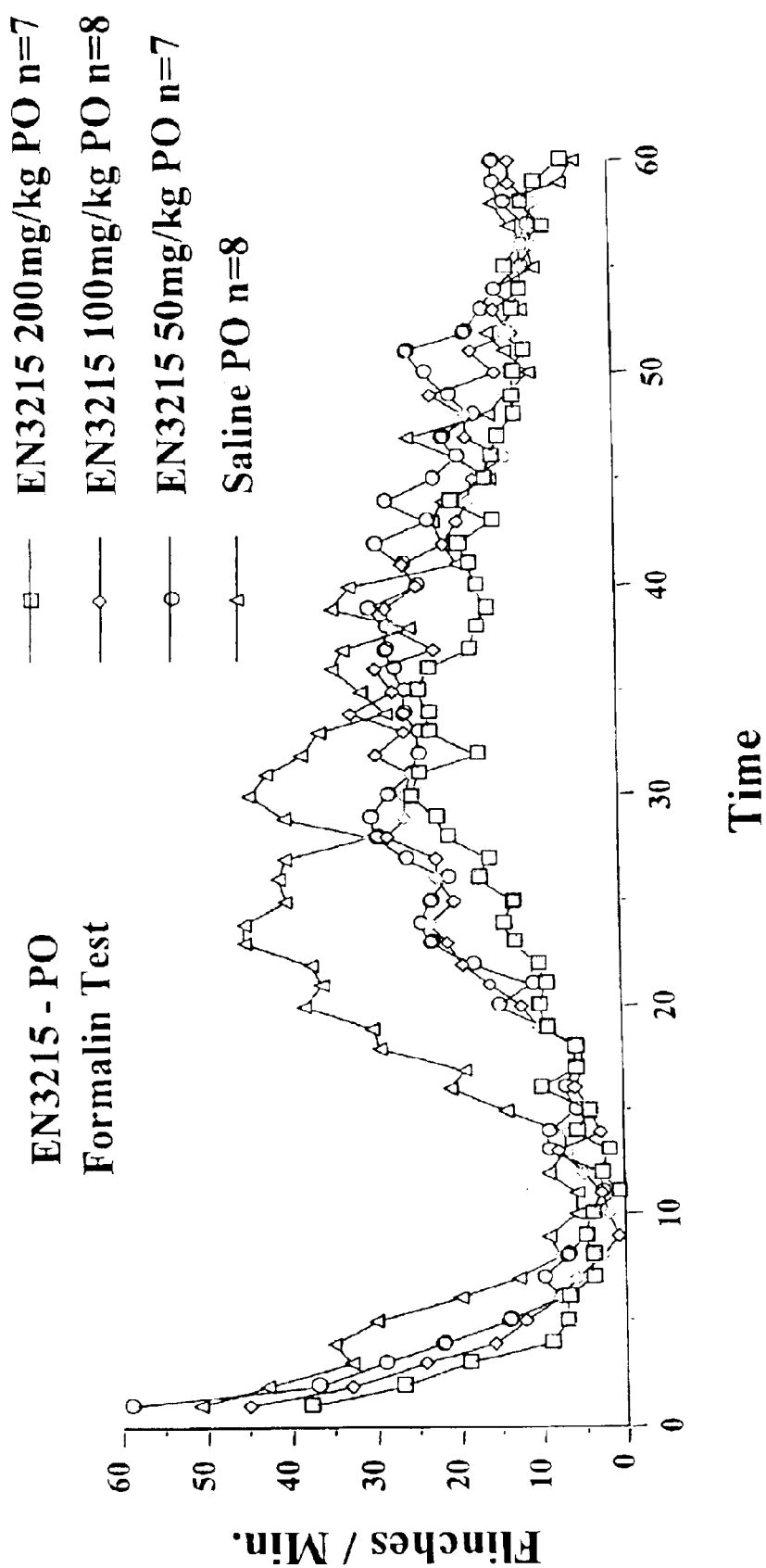

CARBINOLS FOR THE TREATMENT OF NEUROPATHIC DYSFUNCTION

This application claims priority to U.S. Ser. No. 60/329,869, filed on Oct. 16, 2001.

FIELD OF THE INVENTION

This invention describes the use of 4-aryl-4-piperidinecarbinols in the treatment of neuropathic dysfunction and neuropathic pain.

BACKGROUND OF THE INVENTION

Many people, including over three million in the United States alone, experience neuropathic dysfunction. Neuropathic pain associated with neuropathic dysfunction is defined as pain associated with damage or dysfunction of peripheral or central nervous system.

Neuropathic pain is considered a malfunction in the response to a pathologic process occurring along and within the nervous system nociceptive pathways and is a much more complex phenomenon than simple pain. Pain has been defined as "an unpleasant sensory and emotional experience associated with tissue damage or described in terms of such damage."

The most common types of conventional pain are associated with a response to a pathophysiologic process occurring within the tissues, such as inflammation, due to an ongoing injury or damage. The pain signal generates from intact primary afferent nerves that signal noxious events, or nociceptors. Nociceptors can be sensitized by release of algogenic agents (eg, protons, prostaglandins, bradykinin, serotonin, adenosine, cytokines, etc).

In contrast, neuropathic pain is associated with signals generated ectopically and often in the absence of ongoing noxious events by pathologic processes in the peripheral or central nervous system. This dysfunction is associated with common symptoms such as allodynia (pain evoked by normally nonpainful touch), hyperalgesia (abnormally intensive and long-lasting pain from a painful stimuli), intermittent abnormal sensations, and spontaneous, burning, shooting, stabbing, paroxysmal or electrical-sensations.

Neuropathic pain has been associated with sensory changes such as paresthesias (abnormal, intermittent but nonpainful sensations, perceived spontaneously or evoked by a stimulus) or dysesthesias (abnormal painful sensations that are spontaneous or evoked). Allodynia, hyperalgesia and hyperpathia are positive sensory phenomena as opposed to the negative sensory phenomena defined by anesthesia and hypoesthesia. Allodynia, which may be mechanical or thermal, is the painful response to an ordinarily non-noxious stimulus, such as one's clothing, the mere movement of air, touch, or the nonpainful application of a cold or warm stimulus. Hyperalgesias are exaggerated pain responses to a mildly noxious mechanical or thermal stimulus. Hyperpathia may be characterized as a delayed and explosive pain response to a noxious, or at times, non-noxious stimulus.

Neuropathic pain may result from peripheral or central nervous system pathologic events (eg, trauma, ischemia, infections) or from ongoing metabolic or toxic diseases, infections or endocrinologic disorders (eg, diabetes mellitus, diabetic neurophathy, amyloidosis, amyloid polyneuropathy (primary and familial), neuropathies with monoclonal proteins, vasculitic neuropathy, HIV infection, herpes zoster—shingles and postherpetic neuralgia, etc), neuropathy associated with Guillain-Barré syndrome, neuropathy associated with Fabry's disease, entrapment due to anatomic abnormalities, trigeminal and other CNS neuralgias, malignancies, inflammatory conditions or autoimmune disorders (including demyelinating inflammatory disorders, rheumatoid arthritis, systemic lupus erythematosus, Sjögren's syndrome), and cryptogenic causes (idiopathic distal small-fiber neuropathy). Other causes of neuropathic pain include exposure to toxins or drugs (such as aresnic, thallium, alcohol, vincristine, cisplatinum and dideoxynucleosides), dietary or absorption abnormalities, immuno-globulinemias, hereditary abnormalities and amputations (including mastectomy). Neuropathic pain may also result from compression of nerve fibers, such as radiculopathies and carpal tunnel syndrome.

During neuropathic pain, ectopic activity causes a spontaneous discharge in the peripheral nervous system (PNS) pathways, or depending on the location and type of nerve injury, ectopic discharge also may originate in the dorsal-root-ganglion (DRG) cells of damaged afferent axons. Within the same DRG, cell bodies of uninjured axons may exhibit ectopic activity too. Within the central nervous system (CNS), hyperexcitability of the signaling neurons may arise, and other mechanisms that facilitate or distort afferent input are likely. Central mechanisms underlying chronic neuropathic pain are poorly understood. Neuroanatomic, neurophysiologic, and neurochemical changes all occur as a response to PNS or CNS injury. Central sensitization at a dorsal horn level, which is mediated in part via the N-methyl-D-aspartate (NMDA) receptor, is the best characterized change involved in the generation of this dysfunction.

Table 4 below sets out common causes of neuropathic dysfunction. Se generally: www.uspharmacist.com/NewLook/DisplayArticle.cfm?item_num=536).

| Common Etiologies of Neurophatic pain |
| --- |
| Alcohol |
| Diabetes mellitus type 1 and 2 |
| Eosinophilia-myalgia syndrome |
| Guillain-Barre syndrome |
| Heavy metals |
| |
| Arsenic |
| Lead |
| Mercury |
| Thallium |
| HIV/AIDS |
| Malignant tumor-related |
| |
| Medications |
| |
| amiodarone |
| aurothioglucose |
| cisplatinum |
| dapsone |
| d4T (stavudine) |
| ddC (zalcitabine) |
| ddI (didanosine) |
| disulfiram |
| FK 506 |
| hydralazine |
| isoniazid |
| metronidazole |
| nitrofurantoin |
| paclitaxel |
| phenytoin |
| vincristine |
| Monoclonal gammopathies |

| Common Etiologies of Neurophatic pain |
|---|
| Multiple sclerosis |
| Post-stroke central pain |
| Postherpetic neuralgia |
| |
| Traumatic/Compression |
| |
| Carpal tunnel syndrome |
| Radiculopathy (sciatica, etc) |
| Cervical or lumbar radiculopathy |
| Complex regional pain syndrome |
| Spinal cord injury |
| Stump pain |
| Trigeminal neuralgia |
| Vasculitis |
| Vitamin $B_6$ megadosing |
| Vitamin deficiencies ($B_{12}$, $B_1$, $B_6$ and E) |

The treatment of neuropathic pain continues to be a difficult and often unsuccessful medical challenge. For years neuropathic pain has confounded scientists. Drugs for the treatment of standard pain are typically ineffective against neuropathic pain, the drugs for the treatment of neuropathic pain often have no effect on normal pain sensation. Traditional pain treatments, including powerful medications of last resort such as morphine and other opioid analgesics, useful in the treatment of severe pain, rarely alleviate neuropathic pain. The development of tolerance, psychic and physical dependence and potentially serious opioid side effects also limit the usefulness of opioids in treating dysfunction. Anti-inflammatory analgesics, including the Cox-2 inhibitors, lack the efficacy of opioid analgesics and produce other serious side effects including gastrointestinal bleeding and gastric erosion that limits their usefulness in treating neuropathic pain.

Starting in 1988, researchers began to identify animal models that mimic the clinical signs of neuropathic pain. For example, a rat with nerve injuries has been found to exhibit a super-sensitive reaction to a hair tapped on its hindpaw. The rat will quickly jerk away. Some humans with neuropathic pain experience a similarly severe reaction. For them, the tickle of a hair can translate into a long lasting, burning sensation. The animal models of the ailment are helping scientists understand the underlying mechanism of neuropathic pain.

Drugs that have been investigated for the use to treat neuropathic pain include sodium channel antagonists, calcium channel supressors, N-methyl-D-aspartate (NMDA) receptor blockers, anticonvulsant medications, and oral tricyclic antidepressants.

Neurons have many calcium channels, including the high-conductance channel found in the NMDA receptor. Some participate in triggering the release of neurotransmitter from presynaptic vesicles. In chronic constriction injury (CCI) rats, calcium channels are known to affect the spontaneous discharge of injured nociceptive afferents (FIG. 2). However, the drug also exerts its well-known effects on calcium channels in cardiovascular muscle, and the dosages that relieve pain are at or above those causing unacceptable heart-rate and blood-pressure changes.

However, among the many varieties of calcium channels, at least one, the N-type, a voltage-gated channel, occurs only on neurons, not on cardiovascular muscle. In the Philippines, and subsequently at the University of Utah, B. M. Olivera and colleagues studied the venom of poisonous marine snails of the genus Conus. Among hundreds of snail species throughout the Indian and Pacific Oceans, a few survive by hunting fish. Waving a long proboscis, they evidently create the impression of a worm. When a fish investigates, the snail employs the proboscis to sting the fish in the gills. In this way, it introduces a poison directly into the fish's cardiopulmonary circulation. The fish drops dead on the spot. Fractionating this powerful venom, the researchers found it to be a collection of small peptides, each consisting of 13 to 29 amino acids.

Among these substances (classified as omega-conopeptides), the researchers found one that affects the N-type calcium channel. A synthetic replica of a compound from the fish-paralyzing snail venom is one agent that offers relief in these animal models and now also appears to benefit humans. New human studies indicate that low doses of the agent cause minimal side effects and offer relief for patients with neuropathic pain. Under the name SNX-111, it has been synthesized by a biotechnology firm. When applied to the site of sciatic-nerve injury in CCI rats, the treatment reduced heat hyperalgesia and mechanical allodynia for at least three hours, but had no effect on mechanical hyperalgesia. Application to normal nerve had no effect on the animals' responses to any sensory stimuli, thermal or mechanical. Hence, the relief did not represent any anesthetic-like nerve block. Since the boluses were too small for any significant quantities to have diffused to the spinal cord, presynaptic blockade of neurotransmitter release within the dorsal horn was not a tenable explanation, either. Most probably, the SNX compound had reduced spontaneous discharge in primary afferent fibers at and near the site of nerve damage. However, patients cannot take the drug orally, because the stomach digests these agents before they are able to reach the calcium entryways. Instead, physicians administer the agent directly into the spinal cord during a hospital visit. SNX-111 is administered by an implanted pump and catheter that delivers it directly to the lumbar spinal cord.

Other promising agents that can be consumed in pill form incapacitate areas on cells called N-methyl-D-aspartate (NMDA) receptors. Animal models have helped researchers uncover evidence that these receptors share a special relationship with neuropathic pain. It appears that continuous activation of NMDA receptors reorganizes pain-sensing circuits and leads to the super-sensitive quality of neuropathic pain. In a range of animal models studied in numerous laboratories, several different NMDA receptor blockers have significantly reduced neuropathic pain. Limited data amassed from human volunteers suggest a similar effect. Among the drugs is dextrorphan, known pharmacologically as the primary metabolite of the over-the-counter cough suppressant dextromethorphan. When dextrorphan was tested in CCI rats, an intraperitoneal dosage of 25 mg/kg was beneficial against heat hyperalgesia, where it normalized the latency of the withdrawal reflex on the nerve-injured side, but had no effect against mechanical allodynia and caused no changes on the animals' control side.

However, unlike a neurotransmitter receptor that binds acetylcholine or serotonin, the NMDA receptor has binding sites not only for neurotransmitter (glutamate) but also for many other ligands, which modifies the receptor's responsiveness. Indeed, glutamate has no effect unless other conditions are met. The first of these conditions involves a glycine binding site. If the site is unoccupied, the receptor remains inactive. Throughout the CNS, however, the extracellular concentration of glycine seems perennially sufficient to saturate the site. A further hurdle involves magnesium ions. The receptor incorporates a high-conductance ion channel, which in turn can bind $Mg^{2+}$. The binding is voltage-sensitive. If the cell membrane is at its resting bioelectric potential, the ion stays in place, preventing other ions from passing. If, however, the cell has been excited by other inputs, so that the membrane is partially depolarized, the $Mg^{2+}$ is released and ionic currents can flow. The partial depolarization can be accomplished by the cell's excitatory inputs, which, for a dorsal-horn neuron, may include glutamate (received at non-NMDA receptors), acetylcholine, and, among peptide neurotransmitters, substance P and calcitonin gene-related peptide. Inhibitory influences are a similarly long list, including GABA (from local inhibitory neurons), norepinephrine and serotonin (from the brain), and, among neuropeptides, dynorphin and enkephalin. Presumably, exogenous $Mg^{2+}$ keeps NMDA receptors unresponsive to glutamate. Only with glycine present and the membrane partially depolarized, the binding of glutamate to the NMDA receptor can have an effect. The opened ion channel conducts not only $Na^+$, which enters the cell, and $K^+$, which leaves, but also $Ca^{2+}$, which enters.

Because the receptors are important components of a variety of circuits in the brain and spinal cord that carry out different mental functions, blocking their activity also has side effects, such as clouded thinking. The NMDA receptor occurs at a high density in the cerebral cortex and hippocampus. In consequence, drugs that block the receptor can have psychological effects. One strategy has been to identify a relatively ineffective blocker, such that normal mental activity involving NMDA receptors may represent low-frequency discharge at the brain's NMDA synapses and hence may not be affected by a weak receptor blockade. In contrast, neuropathic pain may represent high-frequency discharge, which might be blunted even by a blocker with low affinity for the receptor. Another strategy has been to identify usable differences among NMDA receptor subtypes. So far, at least five have been identified, among which one appears to show a high concentration only in the spinal cord. A drug specific for this spinal subtype might avoid side effects arising from engagement of the brain's NMDA receptors.

In certain respects, epilepsy resembles neuropathic pain. Injured sensory fibers may discharge spontaneously, though with a clocklike regularity unlike the irregular pattern of an epileptiform burst in cortical neurons. In both cases, the discharge is probably due in part to abnormal distribution or activation of voltage-gated sodium channels at the neuronal cell-surface membrane. Therefore, the standard anticonvulsant carbamazepine has been used against neuropathic pain, in particular, tic douloureux, which is one of the rarest of neuropathic syndromes. Against neuropathic pain, as against epilepsy, the drug is thought to have dual modes of action: blockade of sodium channels (in the manner of lidocaine) along with potentiation of GABAergic neurotransmission (in the manner of a barbiturate). Cells utilizing GABA as their inhibitory neurotransmitter are known to affect the dorsal-horn neurons that receive primary sensory afferents and emit ascending fibers. In both neuropathic pain and epilepsy, use of the drug has been impeded by the need to monitor liver function.

New generations of anticonvulsant medications, in particular felbamate, were found to be effective against abnormalities involved in neuropathic pain, at least as modeled in CCI rats. Felbamate is implicated in a voltage-gated sodium-channel blockade, a slight potentiation of GABAergic neurotransmission, and NMDA receptor blockade (owing to its capacity to bind not only glutamate but also NMDA). Nociceptive C fibers are known to use glutamate to signal dorsal-horn neurons, which express NMDA receptors (along with other known types of glutamate receptor). At intraperitoneal doses of up to 600 mg/kg (the drug's antiepileptic range in rats), the high doses completely abolished abnormal sensations in the four measurable ways: heat hyperalgesia, mechanical hyperalgesia, mechanical allodynia and hindpaw guarding. Heat hyperalgesia was tested by noxious heat to the hindpaw. Mechanical hyperalgesia was tested by the tip of a safety pin, pushed slowly until it dimpled the hindpaw skin. Mechanical allodynia was tested by von Frey hairs. All effects lasted two to 12 hours. In the control hindpaw, all responses were unaffected, indicating that the drug acted specifically against neuropathic pain, rather than being broadly analgesic. With only limited solubility in intrathecal media, felbamate could not be tested directly for a spinal site of action. However, the U.S. Food and Drug Administration found that felbamate had been found to cause liver failure and aplastic anemia, sometimes fatally, in humans.

Anticonvulsants, gabapentin and lamotrigine, have been widely used for several years. In CCI rats, gabapentin was tested both intraperitoneally (at 10 to 75 mg/kg) and intrathecally (to the lumbar spinal cord, at 37.5 to 150 mcg/kg). At two and four hours, the intraperitoneal injections suppressed heat hyperalgesia and mechanical allodynia. In some instances, the suppression of heat hyperalgesia was complete. Against mechanical hyperalgesia, the drug lacked effect. At 24 hours, abnormal responses had returned. For the intrathecal injections, the pattern was similar, implying a spinal site of drug action. On the control side, gabapentin, like felbamate, caused no significant change in any responses. Chemically, gabapentin is a small, cyclic GABA analogue. Curiously, it has no direct effect on GABA receptors. Indirect effects have been proposed, for example, an upregulation of intracellular GABA storage. Gabapentin binds with high affinity to a subunit of a voltage-gated calcium channel distributed unevenly throughout the nervous system. It remains uncertain precisely which types of calcium channel have the subunit.

It is widely accepted that oral tricyclic antidepressants (TCAs) are useful adjuncts in treating neuropathic pain. In addition, tricyclic antidepressants may be better tolerated than anticonvulsants. While tricyclic antidepressants are not recognized as primary agents to treat neuropathic pain, TCAs have an effect of serotonin (5-HT) release, the noradrenergic pathways and a sodium channel blocking effect (S. Butler, Adv. Pain Res. Ther. 7:173–197, 1984), with evidence of efficacy existing for amitriptylin, imipramine, desimipramine and clomipramine. This effect is independent of their antidepressant effect and may be dose related. In fact, there is a lack of evidence for efficacy of selective serotonin reuptake inhibitors (SSRI) antidepressants for treating neuropathic pain. Recent work has highlighted a potential effect of topical doxepin, a TCA, in neuropathic pain. The topical application of doxepin is associated with few side effects, and particularly central side-effects.

Venlafaxine has been clinically evaluated for painful diabetic neuropathy (See for example, Pernia, A.; Mico, J. A.; Calderon, E.; Torres, L. M. "Venlafaxine for the treatment of neuropathic pain" *J Pain Symptom Manage*, 2000, 19(6):408–10; Kiayias, J. A.; Vlachou E. D.; Lakka-Papadodima, E. "Venlafaxine HCl in the treatment of painful peripheral diabetic neuropathy" *Diabetes Care*, 2000, 23(5):699; Ansari, A. "The efficacy of newer antidepressants in the treatment of chronic pain: a review of current literature" *Harv Rev Psychiatry* 2000; 7(5):257–77; and Davis, J. L.; Smith, R. L. "Painful peripheral diabetic neuropathy treated with venlafaxine HCl extended release capsules" *Diabetes Care* 1999, 22(11):1909–10).

Despite the research on neuropathic pain to date, very few therapies have been identified that are not associated with significant negative side effects. The research has been made more difficult by the inability to extrapolate success in conventional pain therapy to successful treatment of neuropathic dysfunction and associated pain. Because of neuropathic pains' distinct pathophysiology and response to pharmacotherapy, the FDA considers "neuropathic pain", a unique and stand-alone indication, separate from "chronic pain," "arthritis pain," "migraine pain," and "acute pain." Certain 4-arylpiperidinecarbinols are known to have antidepressant activity. These compounds and methods for preparing them are disclosed in Ciganek, U.S. Pat. No. 4,485, 109, issued Nov. 27, 1984 (E.I. DuPont de Nemours and Company).

4-Aryl-4-piperdine (or pyrrolidine or hexahydroazepine) carbinols and heterocyclic analogs, including 4-(3-thienyl)-α,α,1-trimethyl-4-piperidinemethanol, are disclosed in U.S. Pat. Nos. 5,019,650 and 5,086,063 as compounds useful in the treatment of depression and conventional pain.

U.S. Pat. No. 3,108,111 to Stern et al., Nov. 22, 1963, discloses piperidine compounds useful as cough suppressants and analgesics.

U.S. Pat. No. 3,080,372 to Janssen, Mar. 5, 1963, discloses pharmaceutically useful piperidines.

JP 5,9106-460-A discloses antifungal and analgesic nitrogen containing heterocycles, including piperidines.

BE 775,611 discloses 1-(3,3-diphenyl-1-propyl)-4-arylpiperidines as analgesics, spasmolytics and antitussive agents.

Several secondary piperidinecarbinols have been reported in the literature. Representative of these are M. A. Iorio et al., Tetrahedron, 4983 (1971); F. Bergel et al., J. Chem. Soc., 26, (1944); A. D. MacDonald et al., Brit J. Pharmacol., 1,4 (1946); A. L. Morrison et al., J. Chem. Soc., 1467, (1950); H. Kagi et al., Helv. Chim. Acta, 7,2489 (1949); U. Bondesson et al., Drug Metab. Dispos., 9,376 (1981); U. Bondesson et al., Acta Pharm. Suec., 11, 1 (1980).

Given that neuropathic disorders are chronic, extremely disabling and refractory to currently available analgesics, it would be of great benefit to provide new compositions and methods for its treatment.

Therefore, it is one object of the present invention to provide pharmaceutical compositions for the treatment of neuropathic disorders and associated dysfunction and pain.

It is another embodiment of the present invention to provide methods and uses of compounds and compositions for the treatment of neuropathic pain.

SUMMARY OF THE INVENTION

It has been discovered that 4-(3-thienyl)-α,α,1-trimethyl-4-piperidinemethanol (the compound of formula III, also referred to herein as compound A or EN 3215) or its pharmaceutically acceptable salt or prodrug is a superior compound for the treatment of neuropathic pain, and thus can be used to treat a patient suffering from any symptom arising from this dysfunction. Unlike opioid analgesics, it does not show significant activity at mu, kappa, delta or sigma receptor sites in the brain. Studies in animals show that it lacks the addictive and respiratory depressant properties of narcotic-related analgesics. Unlike anti-inflammatory analgesics, it does not inhibit prostaglandin synthesase activity or show anti-inflammatory effects in vivo. Like the tricyclic antidepressants, it inhibits uptake of serotonin, norepinephrine and/or dopamine in rat brain preparations. Effective doses of the compound of the invention for the treatment of neuropathic pain are not accompanied by significant anticholinergic side effects, sedation or other signs of motor impairment observed with tricyclic antidepressants.

In another embodiment, a compound of the formula (I) is provided for the treatment of neuropathic pain:

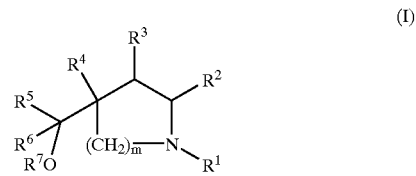

(I)

or its pharmaceutically acceptable salt or prodrug thereof, wherein:
  m is 1, 2 or 3;
  $R^1$ is $CH_3$, $C_2H_5$, n—$C_3H_7$ or allyl;
  $R^2$ and $R^3$ independently are H or alkyl of 1–4 carbon atoms; or $R^1$ and $R^2$ taken together is a branched or unbranched alkylene bridge wherein the bridge is of 3 or 4 carbon atoms; or $R^2$ and $R^3$ taken together is a branched or unbranched alkylene bridge wherein the bridge is of 3 to 6 carbon atoms;
  $R^4$ is:
  (a) phenyl or

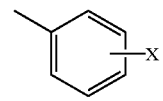

wherein X is one or two substituents, the same or different, selected from F, Cl, Br, perfluoroalkyl, alkyl, alkyl- or dialkylamino, alkylthio, alkoxy or phenoxy, said alkyl in the alkyl-containing groups being of 1 to 12 carbon atoms;
  (b) 2-, 3-, or 4-biphenyl or 2-, 3-, or 4-biphenyl where either or both aromatic groups are substituted with 1 or 2 substituents, the same or different, selected from F, Cl, alkyl, perfluoroalkyl, alkoxy, aryloxy, alkylthio, perfluoroalkoxy, arylthio, perfluoroalkylthio and dialkylamino, said alkyl and alkoxy groups being of 1–12 carbon atoms and said aryl groups being of 6–12 carbon atoms;
  (c) 1- or 2-naphthyl optionally having one or two X substituents as defined in (a) above;
  (d) 2-, 3-, or 4-pyridyl, or 2-, or 3-pyrrolyl optionally substituted with one to three alkyl groups of 1–4 carbon atoms;
  (e) 2- or 3-thienyl optionally substituted with one substituent selected from Cl, Br, or alkyl of 1–4 carbon atoms; or
  (f) 2- or 3-benzothienyl or benzofuryl optionally substituted on the aromatic ring with Cl, Br, or $CF_3$;
  $R^5$ is alkyl of 1–4 carbon atoms, or is taken together with $R^6$ to form a branched or unbranched alkylene bridge of 3–11 carbon atoms;
  $R^6$ is H, alkyl of 1–4 carbon atoms, or is taken together with $R^5$ to form a branched or unbranched alkylene bridge of 3–11 carbon atoms; and
  $R^7$ is H, alkyl of 1–4 carbon atoms, alkanoyl of 1–4 carbon atoms, or —$CH_2$phenyl; or
a pharmaceutically salt or N-oxide thereof, provided that when 1) $R^1$, $R^5$ and $R^6$ are methyl, and $R^2$ and $R^3$ are H, then $R^4$ is not 3,4-$F_2C_6H_3$, 3,4-$Cl_2C_6H_3$, p-t-butylphenyl, 2,3-$(MeO)_2C_6H_3$, 2,5-$(MeO)_2C_6H_3$, or 3-pyridyl;

2) $R^1$ $R^5$ and $R^6$ are methyl or $R^5$ and $R^6$ are taken together as —$(CH_2)_6$— and —$(CH_2)_7$—, then $R^4$ is not 3-$(MeO)C_6H_4$.

Also provided is a novel class of carbinols useful for the treatment of neuropathic pain, having the formula (II):

(II)

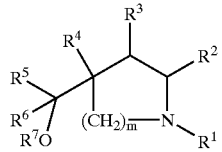

wherein when m is 2 and $R^6$ is other than H, $R^1$ $R^2$ and $R^3$ are as defined above;

$R^4$ is:

(a)

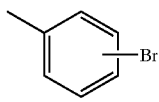

(b) 1-naphthyl optionally substituted with one or two substituents, the same or different, selected from F, Cl, Br; perfluoroalkyl, alkylthio, alkoxy, phenoxy, alkyl, alkyl- or dialkylamino, said alkyl in the alkyl-containing groups being 1–12 carbon atoms.

(c) 3-pyrrolyl optionally substituted with one to three alkyl groups of 1–4 carbon atoms, (d) 2-, or 3-thienyl optionally substituted with Cl, Br, or alkyl of 1–4 carbon atoms, provided when 2-thienyl is substituted with alkyl it is other than the 5-position, or (e) 2-, or 3-benzothienyl or benzofuryl optionally substituted on the aromatic ring with Cl, Br or $CF_3$;

$R^5$ independently is alkyl of 1–4 carbon atoms or when taken together with $R^6$ is a branched or unbranched alkylene bridge of 3–11 carbon atoms;

$R^6$ independently is alkyl of 1–4 carbon atoms, or when taken together with $R^5$ is a branched or unbranched alkylene bridge of 3–11 carbon atoms;

$R^7$ is H, alkyl of 1–4 carbon atoms, alkanoyl, or —$CH_2$phenyl; and when m is 1 or 3, or when $R^6$ is H and m is 2; then $R^1$ independently is $CH_3$, $C_2H_5$, n—$C_3H_7$, or allyl;

$R^2$ and $R^3$ independently are H or alkyl of 1–4 carbon atoms; or $R^1$ and $R^2$ taken together is a branched or unbranched alkylene bridge wherein the bridge is of 3 or 4 carbon atoms;

or $R^2$ and $R^3$ taken together is a branched or unbranched alkylene bridge where the bridge is of 3 to 6 carbon atoms;

$R^4$ is:

(a) phenyl or

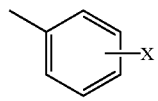

where X is one or two substituents the same or different selected from F, Cl, Br, perfluoroalkyl, alkyl, alkyl- or dialkylamino, alkylthio, alkoxy or phenoxy, said alkyl in the alkyl-containing groups being of 1 to 12 carbon atoms;

(b) 2-, 3-, or 4-biphenyl where either or both aromatic groups are substituted with 1 or 2 substituents, the same or different selected from F, Cl, alkyl, perfluoroalkyl, alkoxy, aryloxy, alkylthio, arylthio, perfluoroalkoxy, perfluoroalkylthio and dialkylamine, amino, said alkyl and alkoxy groups being of 1–12 carbon atoms and said aryl groups being of 6–12 carbon atoms;

(c) 1- or 2-naphthyl optionally having one or two X substituents as defined in (a) above;

(d) 2-, 3-, or 4-pyridyl, or 2-, or 3-pyrrolyl optionally substituted with one to three alkyl groups of 1–4 carbon atoms;

(e) 2- or 3-thienyl optionally substituted with one substituent selected from Cl, Br, or alkyl of 1–4 carbon atoms; or (f) 2- or 3-benzothienyl or benzofuryl optionally substituted on the aromatic ring with Cl, Br, or $CF_3$;

$R^5$ independently is alkyl of 1–4 carbon atoms, or when taken together with $R^6$ is a branched or unbranched alkylene bridge of 3–11 carbon atoms;

$R^6$ independently is H, alkyl of 1–4 carbon atoms, or when taken together with $R^5$ is a branched or unbranched alkylene bridge of 3–11 carbon atoms;

$R^7$ is H, alkyl of 1–4 carbon atoms, alkanoyl, or —$CH_2$phenyl; or a pharmaceutically suitable salt or N-oxide thereof, provided that when $R^6$ is H, $R^1$ is methyl and m is 2, then $R^4$ is other than $C_6H_5$, 2-$(MeO)C_6H_4$, 2,3-$(MeO)_2C_6H_3$ and pharmaceutically suitable salts or N-oxides thereof.

Preferred compounds are those of Formula (1) where when m is 2:

(a) $R^1$ is $CH_3$; or (b) $R^2$ and $R^3$ are H; or (c) $R^4$ is 2- or 3-thienyl, or

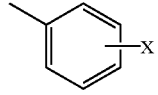

where X is Cl, Br, F, $CF_3$; or (d) $R^5$ is $CH_3$; or (e) $R^6$ is H or $CH_3$; or (f) $R^7$ is H.

Preferred compounds are those of Formula (I) where when m is 1 or 3;

(a) $R^1$ is $CH_3$; or (b) $R^2$, $R^3$ and $R^7$ are H; or (c) R⁴ is

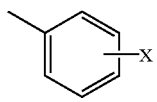

where X is Cl, Br, F or CF₃; or
(d) R⁵ is CH₃; or
(e) R⁶ is H or CH₃.

Specifically preferred compounds are the following:
(a) 4-(3'-Thienyl)-α,α,1-trimethyl-4-piperidinemethanol;
(b) 4-(3'-Chlorophenyl)-α,1-dimethylpiperidinemethanol;
(c) 4-(3'-Chlorophenyl)-α,α,1-trimethyl-4-piperidinemethanol;
(d) 4-(3'-Bromophenyl)-α,1-dimethylpiperidinemethanol;
(e) 4-(3'-Bromophenyl)-α,α,1-trimethyl-4-piperidinemethanol;
(f) 4-(2-Thienyl)-α,1-dimethylpiperidinemethanol;
(g) 4-(3-Thienyl)-α,1-dimethylpiperidinemethanol;
(h) 4-(3'-Chlorophenyl)-α,1-dimethyl-2,3,4,5,6,7-hexahydro-1H-azepine-1-methanol;
(i) 3-(3'-Chlorophenyl)-α,α,1-trimethyl-3-pyrrolidinemethanol; and
(j) 4(4'-Trifluoromethylphenyl)-α-1-dimethylpiperidinemethanol or a pharmaceutically suitable salt thereof.

Also provided is a compound having the formula (III):

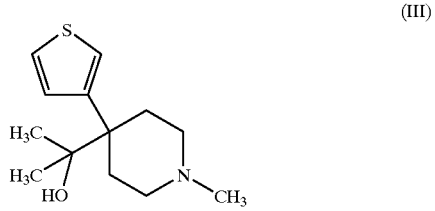

(III)

or its pharmaceutically acceptable salt or prodrug thereof, for the treatment or prophylaxis of neuropathic pain.

Alternatively, provided is a compound having the formula (IV):

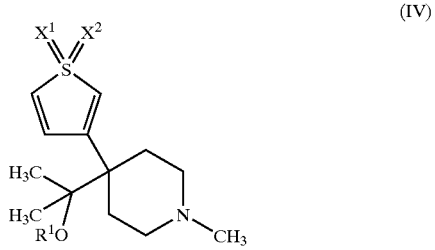

(IV)

or its pharmaceutically acceptable salt or prodrug thereof, wherein:

X¹ and X² are independently O or NR²; and
R¹ is H, alkyl, lower alkyl (such as a $C_1$ to $C_6$ optionally substituted branched or straight-chained alkyl); alkenyl, alkynyl, acyl, —C(O)R⁵, —C(O)NR⁵R⁶, —C(O)OR⁵, —C(O)SR⁵, —C(S)R⁵, —C(S)NR⁵R⁶, —C(S)OR⁵, —C(S)SR⁵, —C(NR⁷)R⁵, —C(NR⁷)NR⁵R⁶, —C(NR⁷)OR⁵, —C(NR⁷)SR⁵ or phosphate; and R², R⁵, R⁶ and R⁷ are independently H, alkyl or lower alkyl (such as a $C_1$ to $C_4$ optionally substituted branched or straight-chained alkyl).

In one embodiment of the present invention, a compound of formula (I)–(IV), optionally in a pharmaceutically acceptable carrier, are used for the treatment or prophylaxis of neuropathic disorders and associated dysfunction and neuropathic pain.

In another embodiment of the invention, compositions comprising compounds of the formula (I)–(IV), optionally in a pharmaceutically acceptable carrier, in combination with one or more other agents are useful for the treatment of neuropathic pain.

In another embodiment of the invention, a method is provided for the treatment or prophylaxis of neuropathic disorder, dysfunction or pain comprising administering to a host, preferably a human, an effective amount of a compound of formula (I)–(IV).

In yet another embodiment of the invention, a method is provided for the treatment or prophylaxis of neuropathic disorder, dysfunction or pain comprising administering to a host, preferably a human, an effective amount of a compound of formula (I)–(IV) in combination or alternation with one or more other active agents.

In yet another embodiment, a use of compounds of the formula (I)–(IV), optionally in a pharmaceutically acceptable carrier, and optionally in combination or alternation with one or more other agents for the treatment or prophylaxis of neuropathic disorder, dysfunction or pain is provided.

In yet another embodiment, a use of compounds of the formula (I)–(IV), optionally in a pharmaceutically acceptable carrier, optionally in combination or alternation with one or more other agents in the manufacture of a medicament for the treatment or prophylaxis of neuropathic pain is provided.

| | Site | Biochemical Change | Anatomic Change |
|---|---|---|---|
| 1. | Sensory periphery | De novo expression of functional receptors (e.g., opioid, alpha-adrenergic) at nociceptive terminals | |
| 2. | Primary afferent neuron with small-diameter, presumably nociceptive, fiber | Decreased synthesis (e.g., of substance P, calcitonin gene-related peptide) Increased synthesis (e.g., of neuropeptide | Sprouting of sympathetic fibers from normal targets (blood vessels) to primary afferent cell bodies |

-continued

| | Site | Biochemical Change | Anatomic Change |
|---|---|---|---|
| | | Y, vasoactive intestinal polypeptide, somatostatin, galanin) | |
| 3. | Primary afferent neuron with large-diameter touch fiber | Increased synthesis (e.g., of substance P, neuropeptide Y) | Sprouting of presynaptic ramifications into superficial dorsal horn, where normally only nociceptors terminate |
| 4. | Dorsal-horn neuron | Increased synthesis (e.g., of opioid peptides) Time-varying changes in opioid receptor classes (micro, delta, kappa) | |
| 5. | Brainstem neuron (dorsal column nuclei) | Responsiveness to substance P released from touch fibers | |

This rewiring helps explain why drugs useful against normal pain are largely ineffective against neuropathic pain, whereas drugs against neuropathic pain are not analgesic (see www.hosppract.com/issues/1998/10/bennett.htm).

Figure 1:
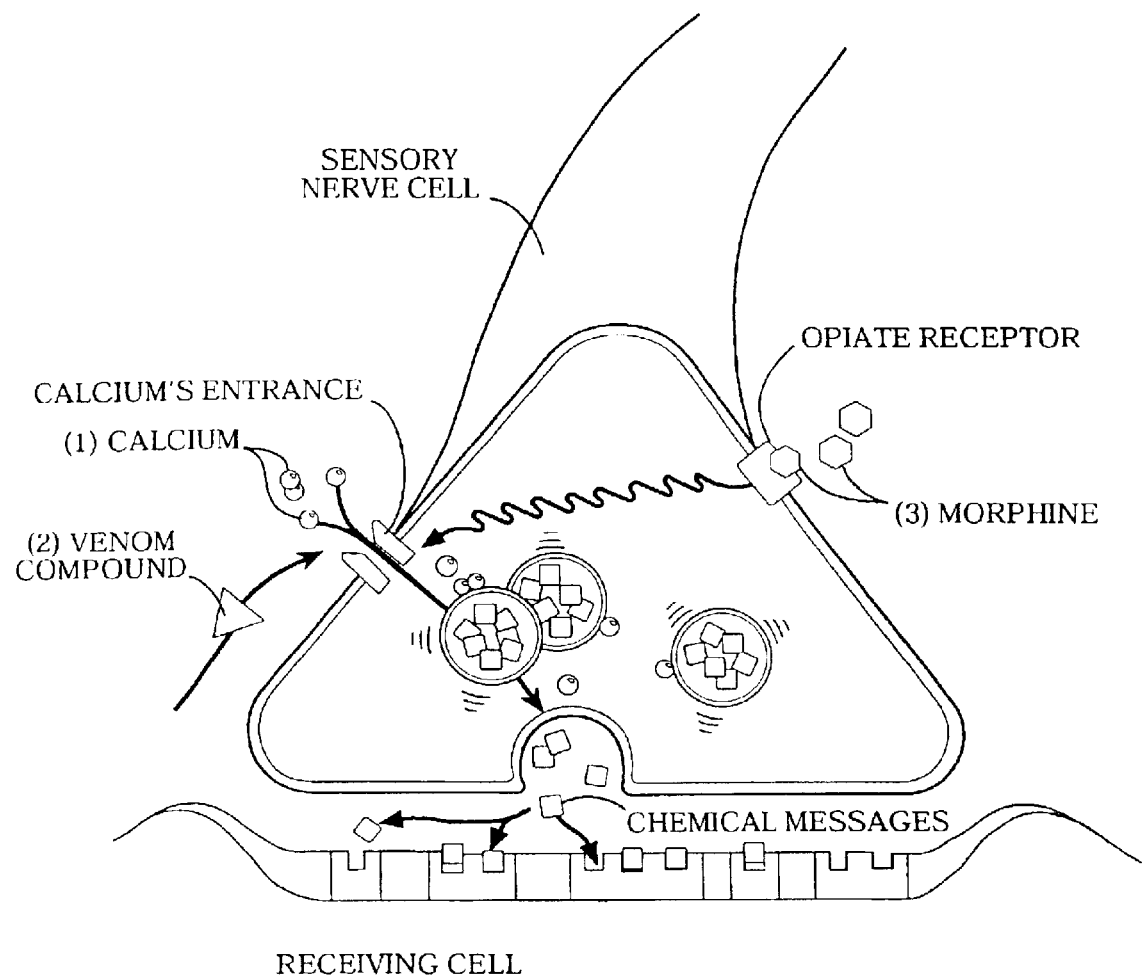
FIG. 1 is an illustration of the anatomic and biochemical rewiring seen in the CNS after nerve injury, indicating that neuropathic pain represents the activity of a sensory processing system at least partly new. In the normal circuitry (top), sensory axons with cell bodies in dorsal root ganglia convey sensation to the spinal cord's dorsal horn, which in turn emits signals via ascending sensory pathways. A representative large-diameter touch fiber has its own ascending branch, while a thinner pain fiber is shown making local spinal connections. After nerve injury, the pain fiber appears to use an altered set of peptides. Meanwhile, substance P begins to appear in touch fibers, which now arborize in dorsal-horn laminae, where their ramifications would not normally occur. See Table below.
Figure 2:
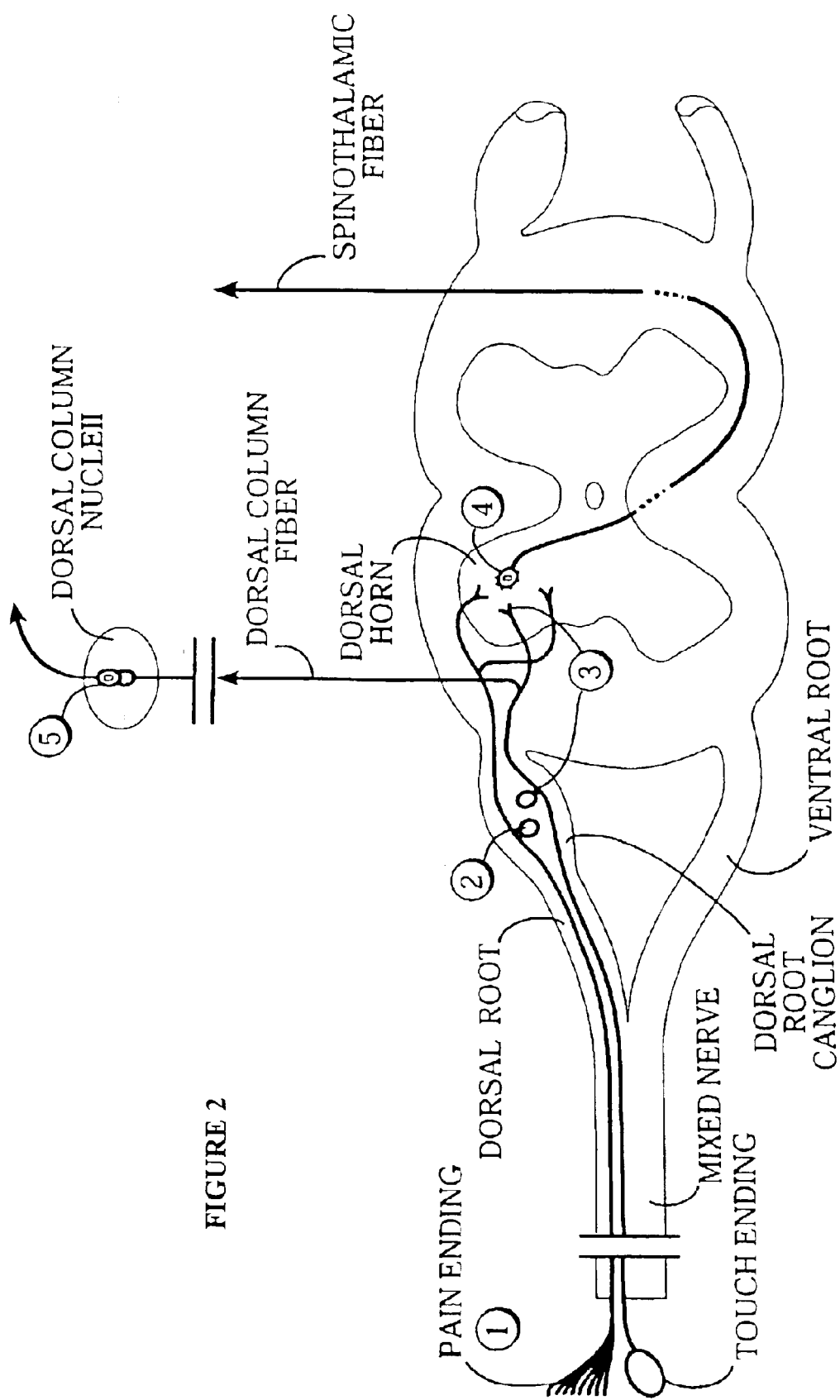

FIG. 2 is an illustration of the receptor implicated in the treatment of neuropathic pain.

Figure 3:
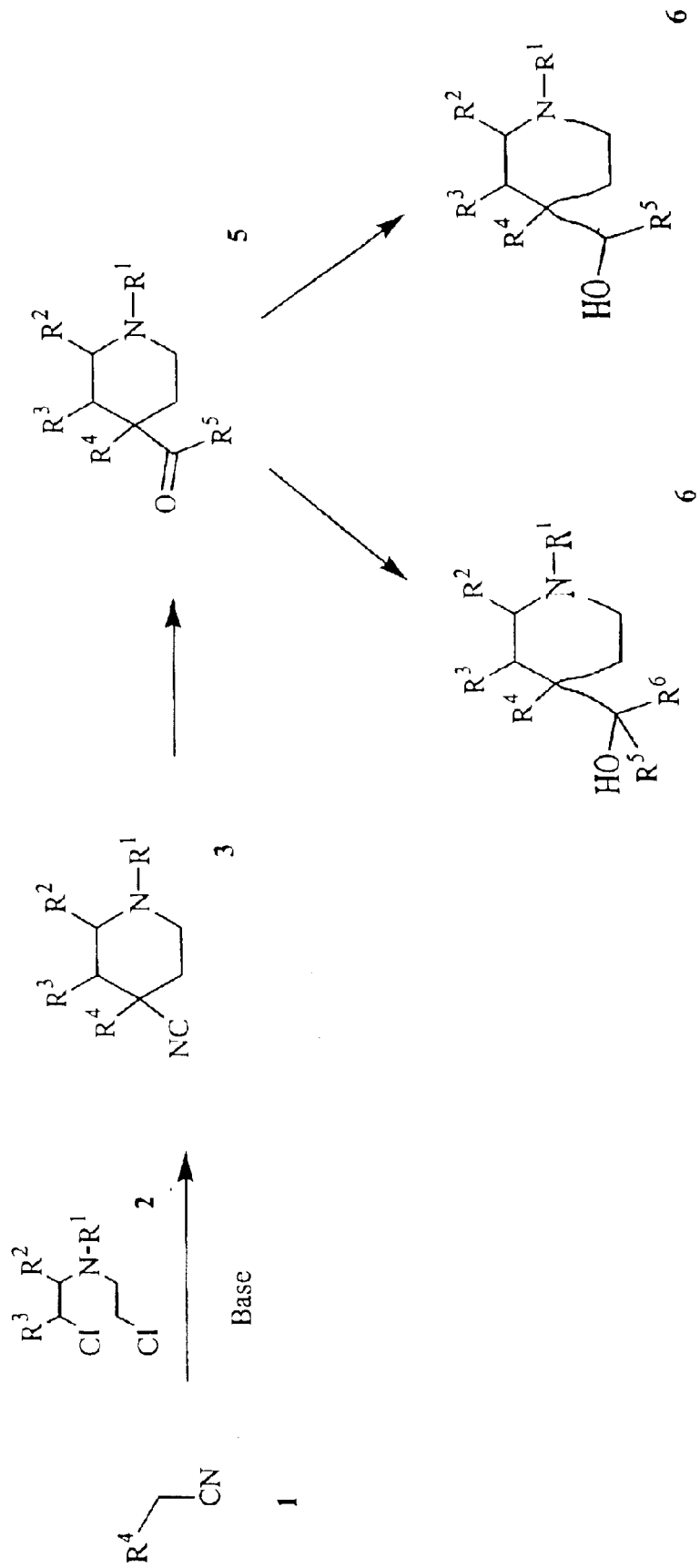

FIG. 3 is a non-limiting example of the synthesis of compounds of the present invention.

Figure 4:
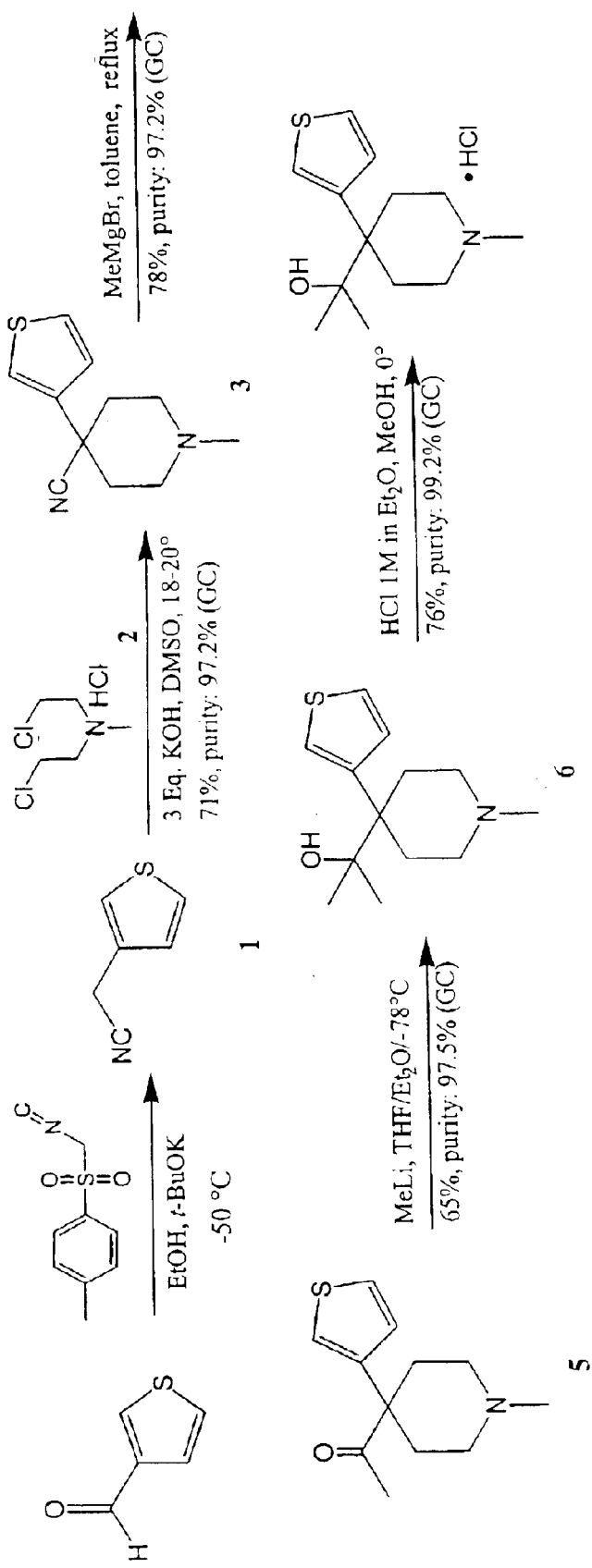

FIG. 4 is a non-limiting example of a preferred embodiment for the synthesis of a compound of the present invention, 4-(3-thienyl)-α,α,1-trimethyl-4-piperidinemethanol.

Figure 5B:
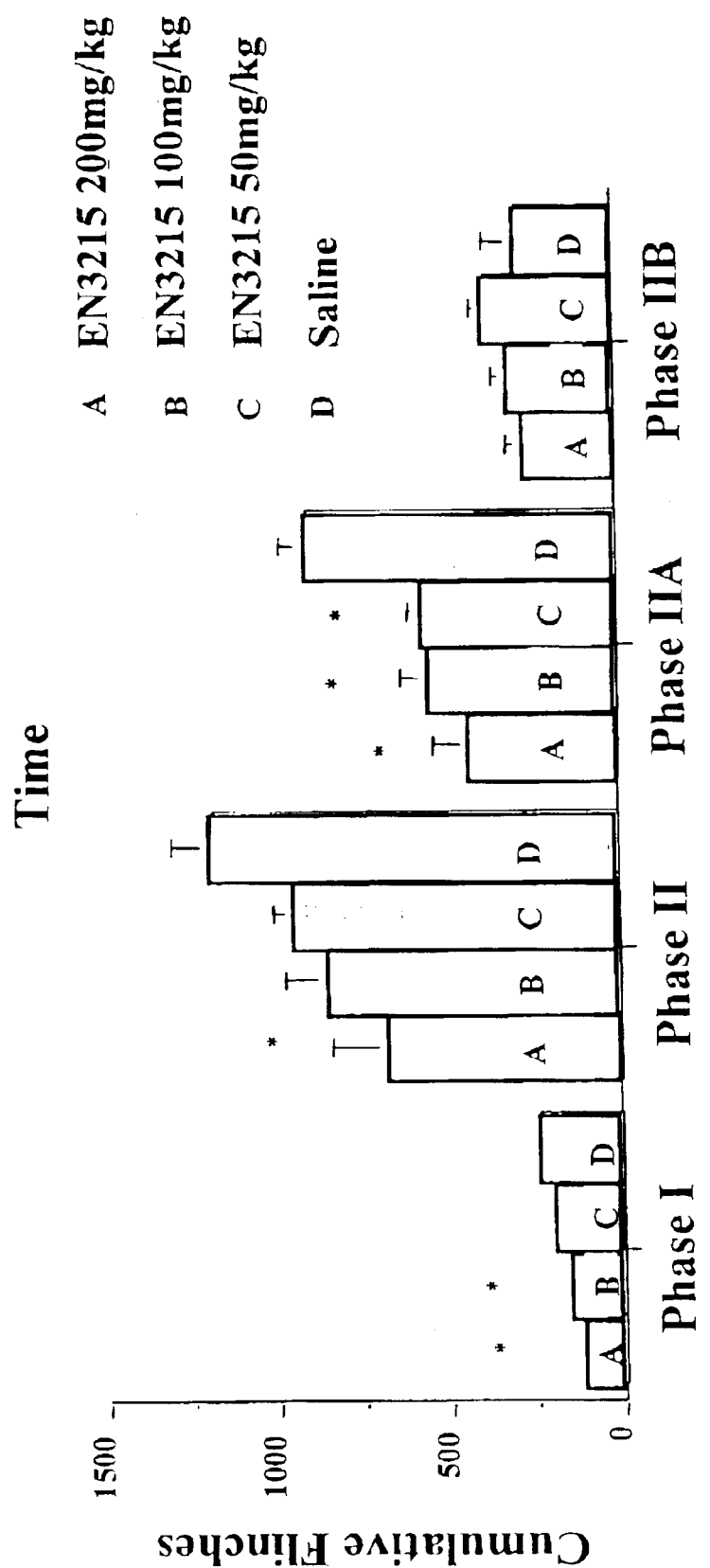
Figure 5C:
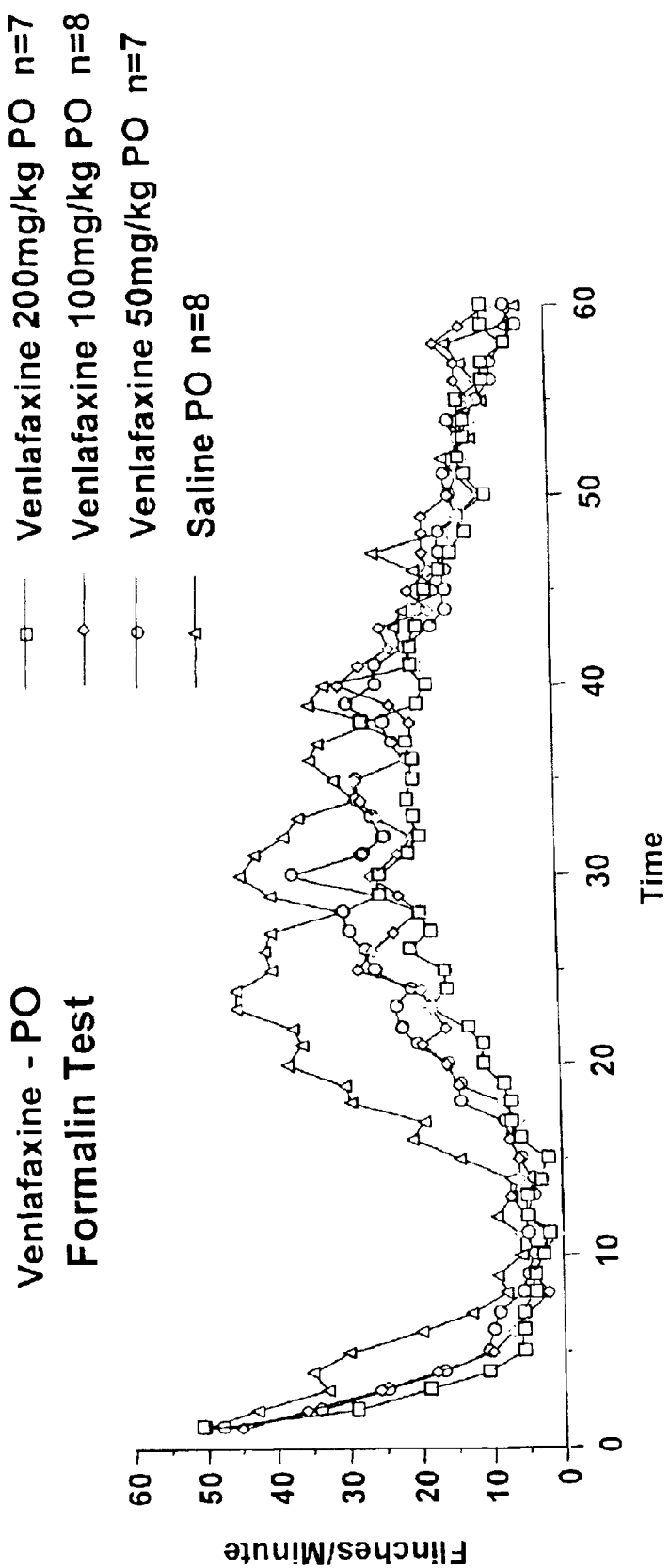
Figure 5D:
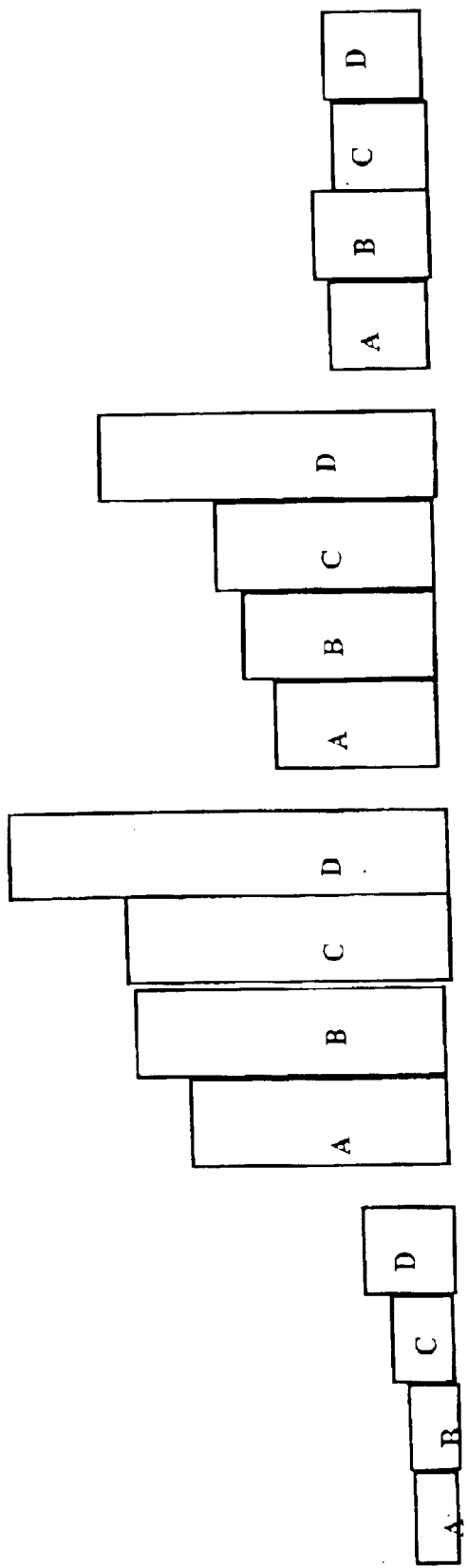
Figure 6A:
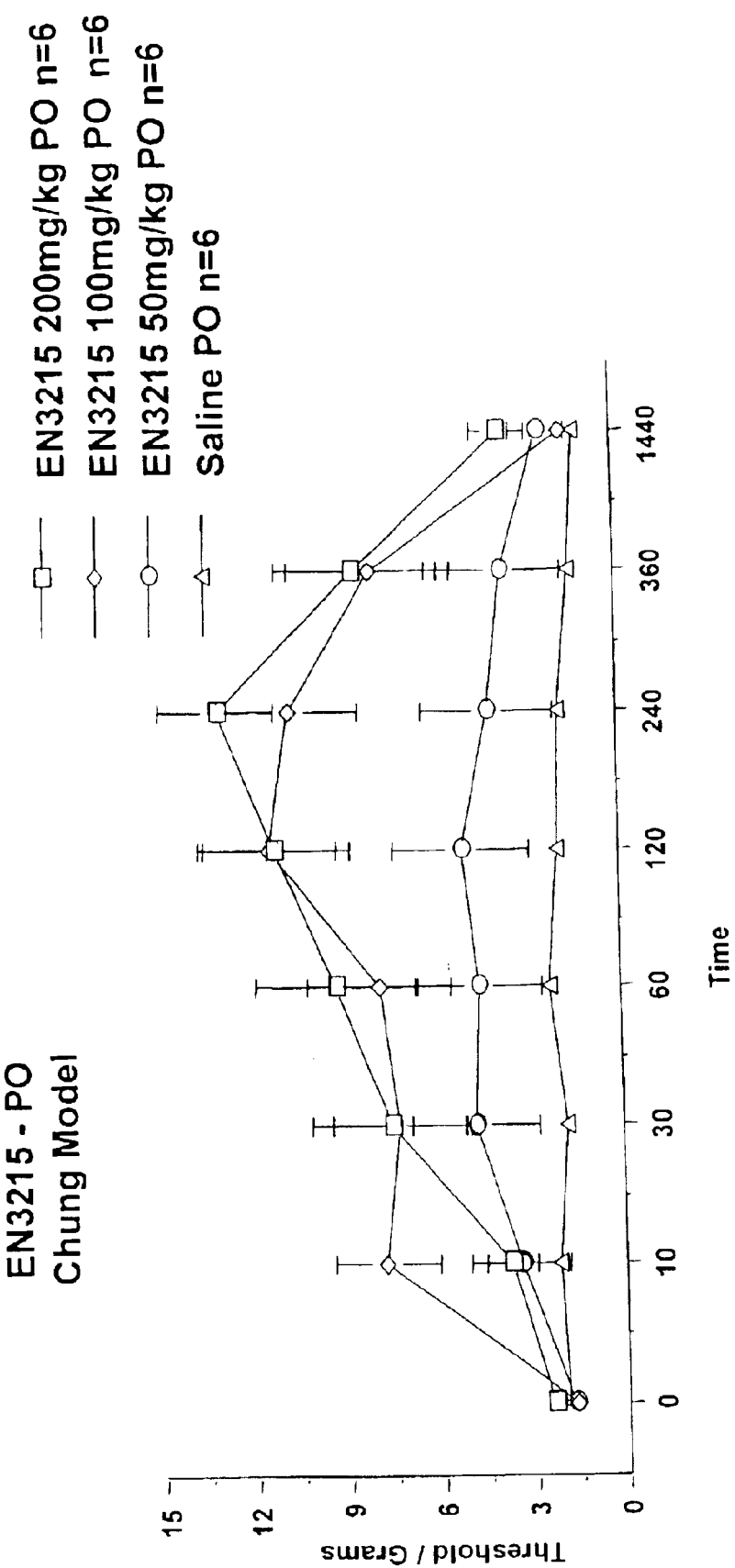
Figure 6B:
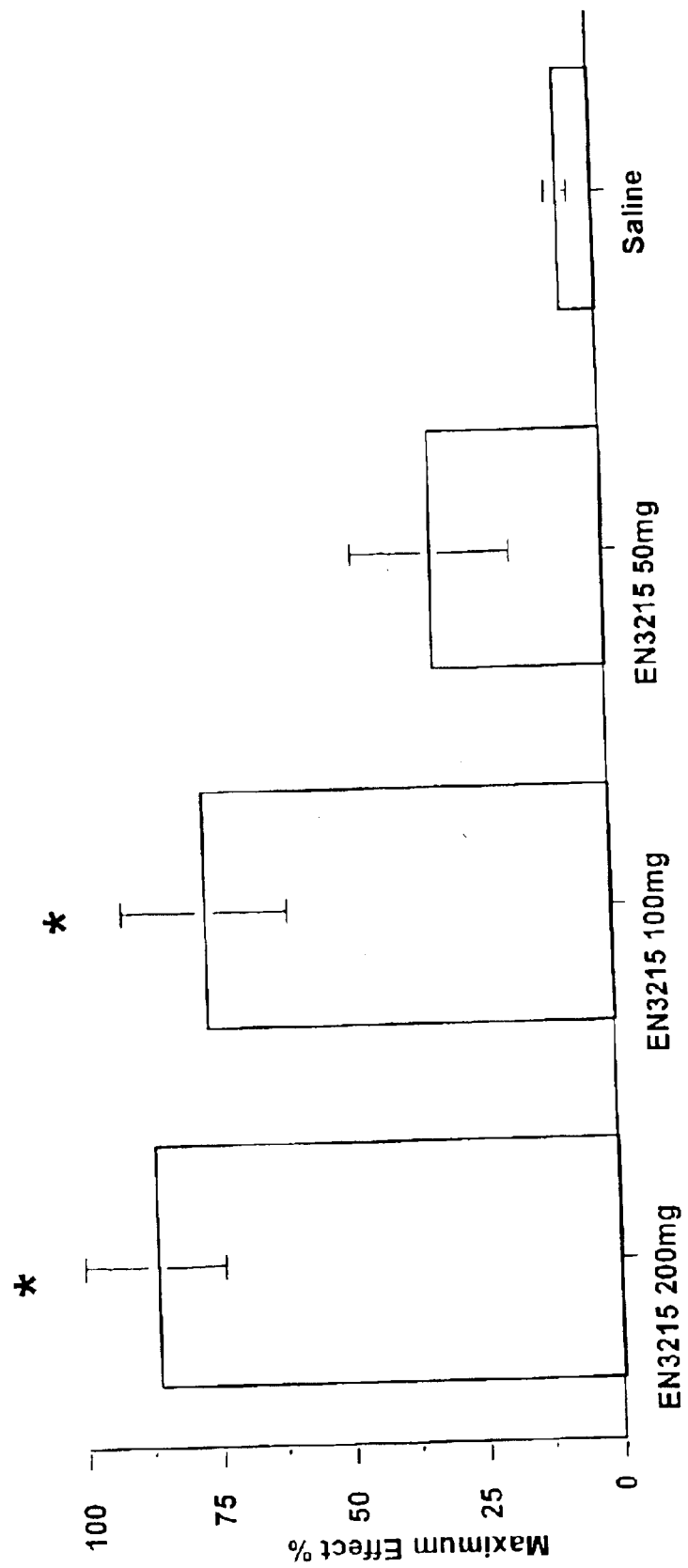
Figure 6C:
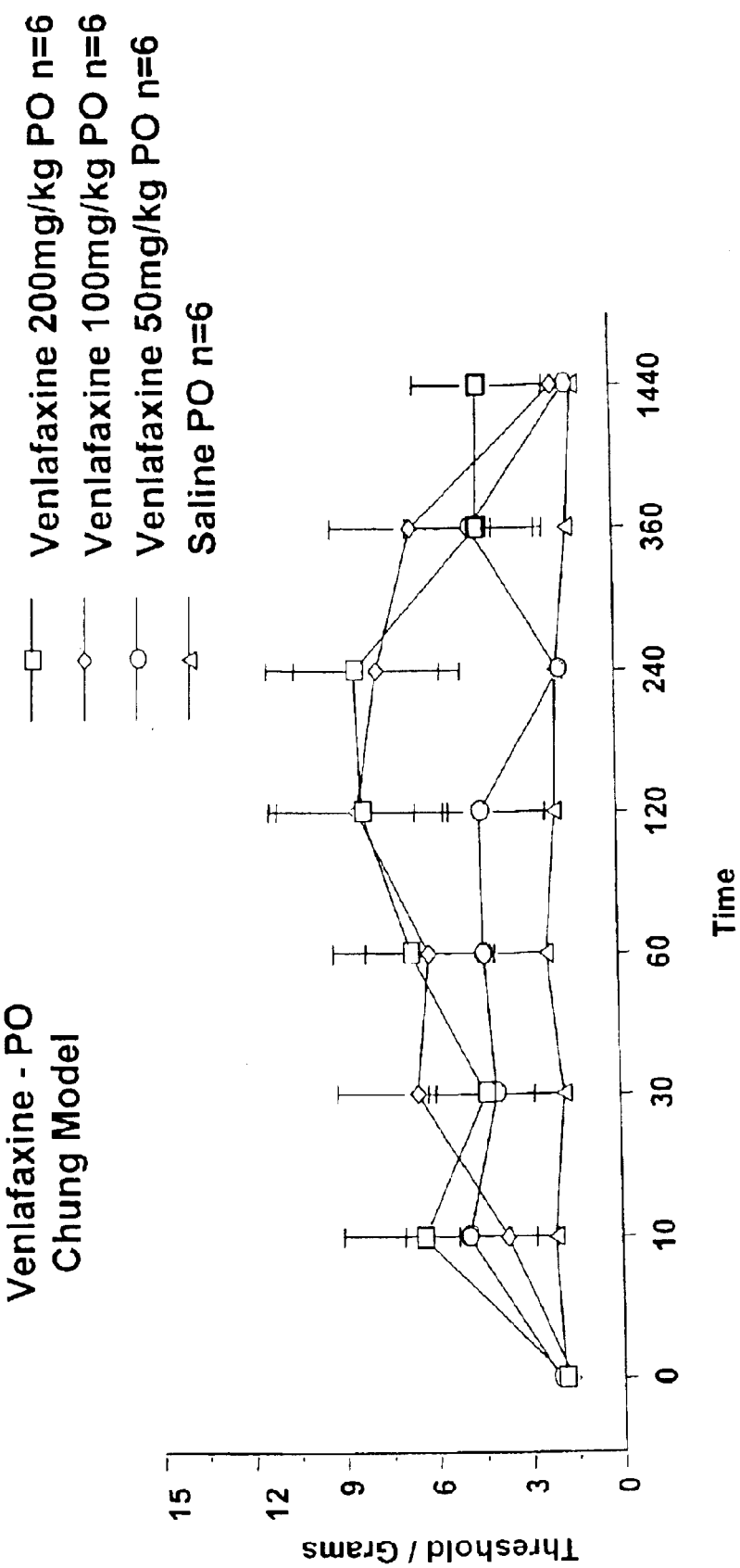
Figure 6D:
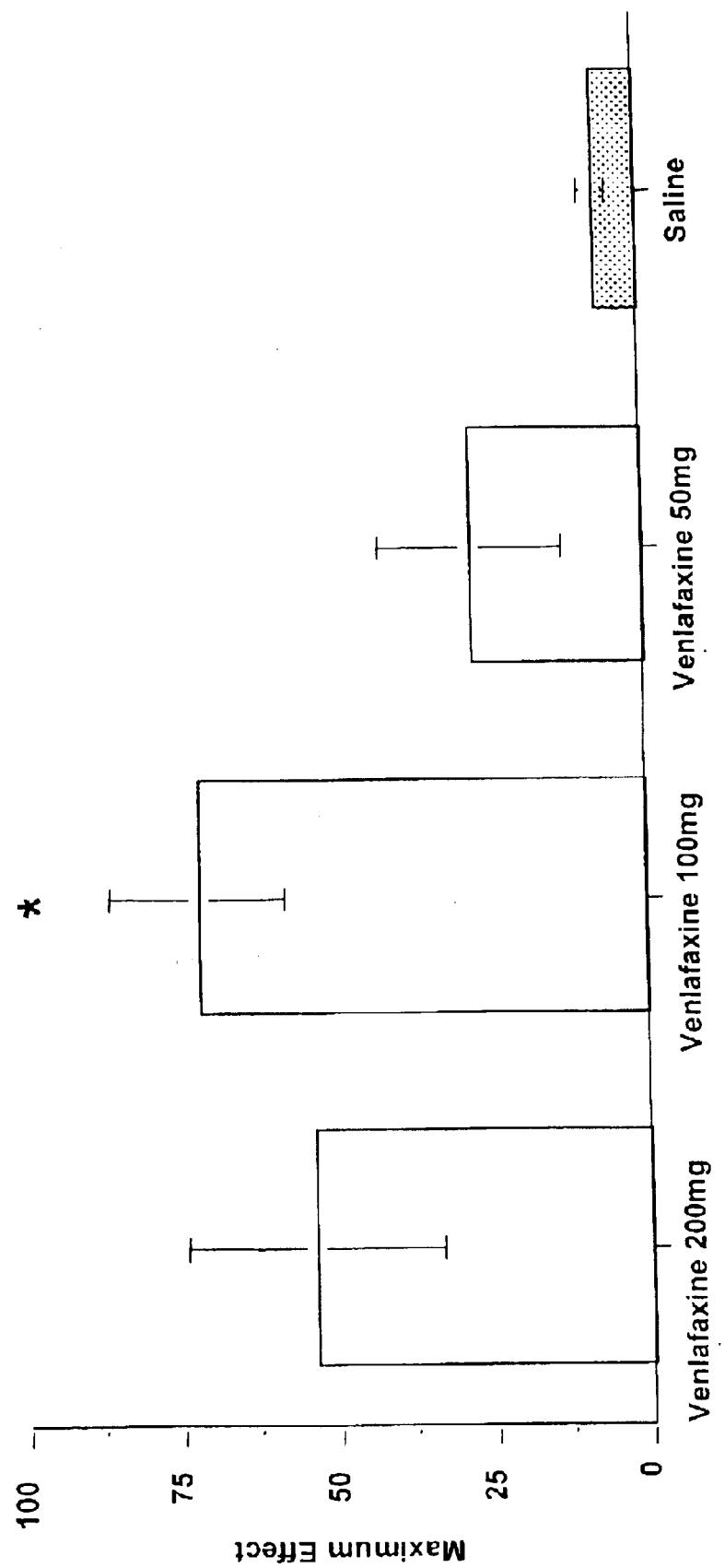

FIG. 5 is an illustration of the efficacy of the compound of the present invention, and in particular of 4-(3-thienyl)-α,α,1-trimethyl-4-piperidinemethanol, in the treatment of neuropathic pain using the formalin model with respect to venlafaxine and a saline control. FIGS. 5A and 5C are line graphs showing the measured flinches per minute over sixty minutes of observation of animals dosed with EN3512 or venlafaxine, respectively. EN3512 and venlafaxine were given at 200 mg/100 mg/50 mg per kg orally and saline was administered as a control. FIGS. 5B and 5D are bar graphs depicting the cumulative measured flinches during the two main phases of the formalin test: phase I—an acute nociceptive component; and phase II—a chronic nociceptive component characterized by hyperalgesia.

FIG. 6 is an illustration of the efficacy of the compound of the present invention, and in particular of 4-(3-thienyl)-α,α,1-trimethyl-4-piperidinemethanol, in the treatment of neuropathic pain using the Chung model with respect to venlafaxine and a saline control. FIGS. 6A and 6C are line graphs showing the increased tactile threshold of the animals at different doses of compound A (200 mg/kg; 100 mg/kg, 50 mg/kg, and saline PO control) and venlafaxine (200 mg/kg; 100 mg/kg; 50 mg/kg; and saline PO control), respectively, over a 24 hour period. FIGS. 6B and 6D are bar graphs depicting the percent maximum effect of drug relative to rats that did not undergo the surgical procedure.

DETAILED DESCRIPTION OF THE INVENTION

It has been discovered that the compound of formulas I–IV, and in particular, 4-(3-thienyl)-α,α, 1-trimethyl-4-piperidinemethanol (the compound of formula III, also referred to herein as compound A or EN3215) or its pharmaceutically acceptable salt or prodrug is a superior compound for the treatment of neuropathic dysfunction and associated pain, and thus can be used to treat a patient suffering from any symptom arising from this dysfunction.

Unlike opioid analgesics, EN3215 does not show significant activity at mu, kappa, delta or sigma receptor sites in the brain. Studies in animals show that it lacks the addictive and respiratory depressant properties of narcotic-related analgesics. Unlike anti-inflammatory analgesics, it does not inhibit prostaglandin synthesase activity or show anti-inflammatory effects in vivo. Like the tricyclic antidepressants, it inhibits uptake of serotonin, norepinephrine and/or dopamine in rat brain preparations. However, effective doses of the compound of the invention for the treatment of neuropathic pain are not accompanied by anticholinergic side effects, sedation or other signs of motor impairment observed with tricyclic antidepressants.

In one embodiment, compounds of the present invention, optionally in a pharmaceutically acceptable carrier, are used for the treatment or prophylaxis of neuropathic dysfunction or pain.

In another embodiment of the invention, compositions comprising compounds of the present invention, optionally in a pharmaceutically acceptable carrier, in combination with one or more other agents are useful for the treatment of neuropathic dysfunction or pain.

In another embodiment of the invention, a method is provided for the treatment or prophylaxis of neuropathic dysfunction or pain comprising administering to a host, preferably a human, an effective amount of a compounds of the present invention.

In yet another embodiment of the invention, a method is provided for the treatment or prophylaxis of neuropathic dysfunction or pain comprising administering to a host, preferably a human, an effective amount of a compounds of the present invention in combination or alternation with one or more other agents are useful for the treatment of neuropathic pain.

In yet another embodiment, use of the compound of the present invention, optionally in a pharmaceutically acceptable carrier, and optionally in combination or alternation with one or more other agents for the treatment or prophylaxis of neuropathic dysfunction or pain is provided.

In yet another embodiment, use of the compound of the present invention, optionally in a pharmaceutically acceptable carrier, and optionally in combination or alternation with one or more other agents in the manufacture of a medicament for the treatment or prophylaxis of neuropathic dysfunction or pain is provided.

I. Active Compounds of the Invention

The invention includes a compound of the formula:

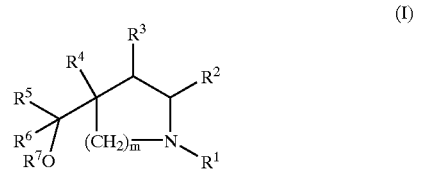
(I)

or its pharmaceutically acceptable salt or prodrug thereof, wherein:

m is 1, 2 or 3;

$R^1$ is $CH_3$, $C_2H_5$, n—$C_3H_7$ or allyl;

$R^2$ and $R^3$ independently are H or alkyl of 1–4 carbon atoms; or $R^1$ and $R^2$ taken together is a branched or unbranched alkylene bridge wherein the bridge is of 3 or 4 carbon atoms; or $R^2$ and $R^3$ taken together is a branched or unbranched alkylene bridge wherein the bridge is of 3 to 6 carbon atoms;

$R^4$ is:

(g) phenyl or

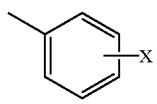

wherein X is one or two substituents, the same or different, selected from F, Cl, Br, perfluoroalkyl, alkyl, alkyl- or dialkylamino, alkylthio, alkoxy or phenoxy, said alkyl in the alkyl-containing groups being of 1 to 12 carbon atoms;

(h) 2-, 3-, or 4-biphenyl or 2-, 3-, or 4-biphenyl where either or both aromatic groups are substituted with 1 or 2 substituents, the same or different, selected from F, Cl, alkyl, perfluoroalkyl, alkoxy, aryloxy, alkylthio, perfluoroalkoxy, arylthio, perfluoroalkylthio and dialkylamino, said alkyl and alkoxy groups being of 1–12 carbon atoms and said aryl groups being of 6–12 carbon atoms;

(i) 1- or 2-naphthyl optionally having one or two X substituents as defined in (a) above;

(j) 2-, 3-, or 4-pyridyl, or 2-, or 3-pyrrolyl optionally substituted with one to three alkyl groups of 1–4 carbon atoms;

(k) 2- or 3-thienyl optionally substituted with one substituent selected from Cl, Br, or alkyl of 1–4 carbon atoms; or (l) 2- or 3-benzothienyl or benzofuryl optionally substituted on the aromatic ring with Cl, Br, or $CF_3$;

$R^5$ is alkyl of 1–4 carbon atoms, or is taken together with $R^6$ to form a branched or unbranched alkylene bridge of 3–11 carbon atoms;

$R^6$ is H, alkyl of 1–4 carbon atoms, or is taken together with $R^5$ to form a branched or unbranched alkylene bridge of 3–11 carbon atoms; and $R^7$ is H, alkyl of 1–4 carbon atoms, alkanoyl of 1–4 carbon atoms, or —$CH_2$phenyl; or a pharmaceutically salt or N-oxide thereof, provided that when 3) $R^1$ $R^5$ and $R^6$ are methyl, and $R^2$ and $R^3$ are H, then $R^4$ is not 3,4-$F_2C_6H_3$, 3,4-$Cl_2C_6H_3$, p-t-butylphenyl, 2,3-$(MeO)_2C_6H_3$, 2,5-$(MeO)_2C_6H_3$, or 3-pyridyl;

4) $R^1$, $R^5$ and $R^6$ are methyl or $R^5$ and $R^6$ are taken together as —$(CH_2)_6$— and —$(CH_2)_7$—, then $R^4$ is not 3-$(MeO)C_6H_4$.

Also provided is a novel class of carbinols useful for the treatment of neuropathic pain, having the formula (II):

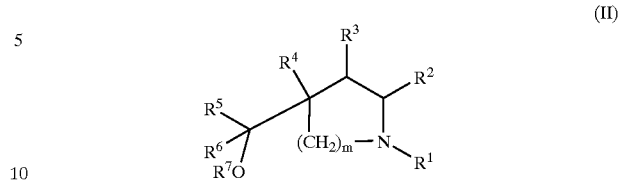
(II)

wherein when m is 2 and $R^6$ is other than H, $R^1$, $R^2$ and $R^3$ are as defined above;

$R^4$ is:

(f)

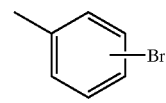

(g) 1-naphthyl optionally substituted with one or two substituents, the same or different, selected from F, Cl, Br; perfluoroalkyl, alkylthio, alkoxy, phenoxy, alkyl, alkyl- or dialkylamino, said alkyl in the alkyl-containing groups being 1–12 carbon atoms.

(h) 3-pyrrolyl optionally substituted with one to three alkyl groups of 1–4 carbon atoms, (i) 2-, or 3-thienyl optionally substituted with Cl, Br, or alkyl of 1–4 carbon atoms, provided when 2-thienyl is substituted with alkyl it is other than the 5-position, or (j) 2-, or 3-benzothienyl or benzofuryl optionally substituted on the aromatic ring with Cl, Br or $CF_3$;

$R^5$ independently is alkyl of 1–4 carbon atoms or when taken together with $R^6$ is a branched or unbranched alkylene bridge of 3–11 carbon atoms;

$R^6$ independently is alkyl of 1–4 carbon atoms, or when taken together with $R^5$ is a branched or unbranched alkylene bridge of 3–11 carbon atoms;

$R^7$ is H, alkyl of 1–4 carbon atoms, alkanoyl, or —$CH_2$phenyl; and when m is 1 or 3, or when $R^6$ is H and m is 2; then $R^1$ independently is $CH_3$, $C_2H_5$, n—$C_3H_7$, or allyl;

$R^2$ and $R^3$ independently are H or alkyl of 1–4 carbon atoms; or $R^1$ and $R^2$ taken together is a branched or unbranched alkylene bridge wherein the bridge is of 3 or 4 carbon atoms;

or $R^2$ and $R^3$ taken together is a branched or unbranched alkylene bridge where the bridge is of 3 to 6 carbon atoms;

$R^4$ is:

(g) phenyl or

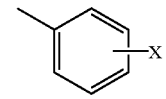

where X is one or two substituents the same or different selected from F, Cl, Br, perfluoroalkyl, alkyl, alkyl- or dialkylamino, alkylthio, alkoxy or phenoxy, said alkyl in the alkyl-containing groups being of 1 to 12 carbon atoms;

(h) 2-, 3-, or 4-biphenyl where either or both aromatic groups are substituted with 1 or 2 substituents, the same or different selected from F, Cl, alkyl, perfluoroalkyl, alkoxy, aryloxy, alkylthio, arylthio, perfluoroalkoxy, perfluoroalkylthio and dialkylamine, amino, said alkyl and alkoxy groups being of 1–12 carbon atoms and said aryl groups being of 6–12 carbon atoms;

(i) 1- or 2-naphthyl optionally having one or two X substituents as defined in (a) above;

(j) 2-, 3-, or 4-pyridyl, or 2-, or 3-pyrrolyl optionally substituted with one to three alkyl groups of 1–4 carbon atoms;

(k) 2- or 3-thienyl optionally substituted with one substituent selected from Cl, Br, or alkyl of 1–4 carbon atoms; or (l) 2- or 3-benzothienyl or benzofuryl optionally substituted on the aromatic ring with Cl, Br, or $CF_3$;

$R^5$ independently is alkyl of 1–4 carbon atoms, or when taken together with $R^6$ is a branched or unbranched alkylene bridge of 3–11 carbon atoms;

$R^6$ independently is H, alkyl of 1–4 carbon atoms, or when taken together with $R^5$ is a branched or unbranched alkylene bridge of 3–11 carbon atoms;

$R^7$ is H, alkyl of 1–4 carbon atoms, alkanoyl, or —$CH_2$phenyl; or a pharmaceutically suitable salt or N-oxide thereof, provided that when $R^6$ is H, $R^1$ is methyl and m is 2, then $R^4$ is other than $C_6H_5$, 2-(MeO)$C_6H_4$, 2,3-(MeO)$_2C_6H_3$ and pharmaceutically suitable salts or N-oxides thereof.

Preferred compounds are those of Formula (I) where when m is 2:

(g) $R^1$ is $CH_3$; or (h) $R^2$ and $R^3$ are H; or (i) $R^4$ is 2- or 3-thienyl, or

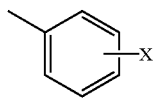

where X is Cl, Br, F, $CF_3$; or (j) $R^5$ is $CH_3$; or (k) $R^6$ is H or $CH_3$; or (l) $R^7$ is H.

Preferred compounds are those of Formula (I) where when m is 1 or 3;

(f) $R^1$ is $CH_3$; or (g) $R^2$, $R^3$ and $R^7$ are H; or (h) $R^4$ is

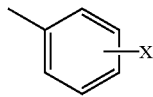

where X is Cl, Br, F or $CF_3$; or (i) $R^5$ is $CH_3$; or (j) $R^6$ is H or $CH_3$.

Specifically preferred compounds are the following:

(a) 4-(3'-Thienyl)-α,α,1-trimethyl-4-piperidinemethanol;

(b) 4-(3'-Chlorophenyl)-α,1-dimethylpiperidinemethanol;

(c) 4-(3'-Chlorophenyl)-α,α,1-trimethyl-4-piperidinemethanol;

(d) 4-(3'-Bromophenyl)-α,1-dimethylpiperidinemethanol;

(e) 4-(3'-Bromophenyl)-α,α,1-trimethyl-4-piperidinemethanol;

(f) 4-(2-Thienyl)-α,1-dimethylpiperidinemethanol;

(g) 4-(3-Thienyl)-α,1-dimethylpiperidinemethanol;

(h) 4-(3'-Chlorophenyl)-α,1-dimethyl-2,3,4,5,6,7-hexahydro-1H-azepine-1-methanol;

(i) 3-(3'-Chlorophenyl)-α,α,1-trimethyl-3-pyrrolidinemethanol; and (j) 4(4'-Trifluoromethylphenyl)-α-1-dimethylpiperidinemethanol or a pharmaceutically suitable salt thereof.

Also provided is a compound having the formula (III):

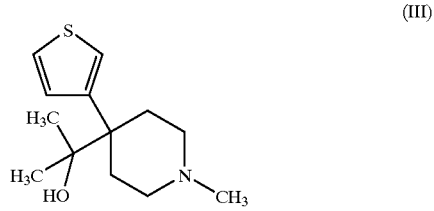

or its pharmaceutically acceptable salt or prodrug thereof, for the treatment or prophylaxis of neuropathic pain.

Alternatively, provided is a compound having the formula (IV):

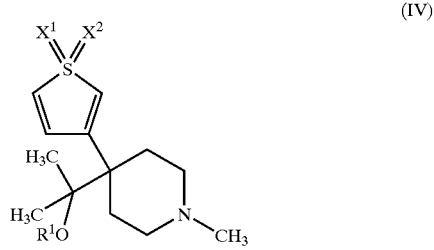

or its pharmaceutically acceptable salt or prodrug thereof, wherein:

$X^1$ and $X^2$ are independently O or $NR^2$; and $R^1$ is H, alkyl, lower alkyl (such as a $C_1$ to $C_6$ optionally substituted branched or straight-chained alkyl); alkenyl, alkynyl, acyl, —$C(O)R^5$, —$C(O)NR^5R^6$, —$C(O)OR^5$, —$C(O)SR^5$, —$C(S)R^5$, —$C(S)NR^5R^6$, —$C(S)OR^5$, —$C(S)SR^5$, —$C(NR^7)R^5$, —$C(NR^7)NR^5R^6$, —$C(NR^7)OR^5$, —$C(NR^7)SR^5$ or phosphate; and $R^2$, $R^5$, $R^6$ and $R^7$ are independently H, alkyl or lower alkyl (such as a $C_1$ to $C_4$ optionally substituted branched or straight-chained alkyl).

II. Definitions

The term "alkyl," as used herein, unless otherwise specified, refers to a saturated straight, branched, or cyclic, primary, secondary, or tertiary hydrocarbon, including but not limited to those of $C_1$ to $C_{16}$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl.

The alkyl group can be optionally substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, thiol, imine, sulfonic acid, sulfate, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term lower alkyl, as used herein, and unless otherwise specified, refers to a $C_1$ to $C_6$ saturated straight, branched, or if appropriate, a cyclic (for example, cyclopropyl) alkyl group, including both substituted and unsubstituted forms. Some non-limiting examples include methyl, (cyclopropyl) methyl, (cyclobutyl)methyl, (cyclopentyl)methyl, ethyl, 1-cyclopropyl-ethyl, 2-cyclopropylethyl, 1-cyclobutylethyl, 2-cyclobutylethyl, propyl, isopropyl, 1-(cyclo-propyl) propyl, 2-(cyclopropyl)propyl, 3-(cyclopropyl)propyl, cyclopropyl, methylcyclopropyl, 2,2-dimethylcyclopropyl, 1,2-dimethylcyclopropyl, ethylcyclopropyl, propylcyclopropyl, 1-ethyl-1-methylcyclopropyl, 1-ethyl-2-methylcyclopropyl, 1,1,2-trimethylcyclopropyl, 1,2,3-trimethylcyclopropyl, butyl, isobutyl, t-butyl, sec-butyl, 2,2-dimethylbutyl, 2,3-dimethylbutyl, cyclobutyl, methylcyclobutyl, 1,1-dimethylcyclobutyl, 1,2-dimethylcyclobutyl, 1,3-dimethylcyclobutyl, ethylcyclobutyl, pentyl, isopentyl, neopentyl, 2-methylpentyl, 3-methylpentyl, cyclopentyl, methylcyclopentyl, spiropentyl, methylspiropentyl, hexyl, isohexyl and cyclohexyl.

The term alkylene refers to a saturated hydrocarbyldiyl radical of straight or branched configuration, including but not limited to those that have from one to ten carbon atoms. Included within the scope of this term are methylene, 1,2-ethane-diyl, 1,1-ethane-diyl, 1,3-propane-diyl, 1,2-propane-diyl, 1,3-butane-diyl, 1,4-butane-diyl and the like.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The term "neuropathic dysfunction" refers to any malfunction in the response to a pathologic process occurring along and within the nervous system nociceptive pathways. As nonlimiting examples, neuropathic pain refers to the dysfunction associated with the following conditions (see www.postgradmed.com/issues/1999/11_99/neuropathic.htm).

| Condition | Type or distribution of dysfunction |
|---|---|
| Diabetes | Peripheral neuropathy |
|  | Mononeuropathy |
|  | Radiculopathy |
| HIV infection or AIDS | Peripheral neuropathy |
|  | Mononeuropathy |
|  | Radiculopathy |
|  | Myelopathy |
| Multiple sclerosis | Myelopathy |
|  | Trigeminal neuralgia |
|  | Scattered nerve pain |
| Cancer chemotherapy | Peripheral neuropathy |
| Spine surgery | Radiculopathy |
| Alcoholism with neuropathy | Peripheral neuropathy |
|  | Mononeuropathy |
| Herpes zoster | Radiculopathy (dermatome) |
| Amputation | Neuroma |
|  | Phantom limb |

The term host refers to animals, in particular, mammals, primates and humans. In most animal applications of the present invention, the host is a human patient. Veterinary applications, in certain indications, however, are included by the present invention.

The term "pharmaceutically acceptable salt or prodrug" is used throughout the specification to describe any pharmaceutically acceptable form (such as an ester, phosphate ester, salt of an ester or a related group) of an active compound which, upon administration to a patient, provides the active compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include, but are not limited to, compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. The compounds of this invention are effective for the treatment or prophylaxis of neuropathic pain, or are metabolized to a compound that exhibits such activity.

III. Combination and Alternation Therapies

Therapy for the treatment of neuropathic pain can be augmented with or with without increasing dosage, via combination and/or alternation therapy with another active agent that treats the same or a different indication. In general, in combination therapy, effective dosages of two or more agents are administered together, whereas during alternation therapy, an effective dosage of each agent is administered serially. The dosage will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of agents that can be used in combination or alternation with the compounds of the present invention include the following.

| Drug | Class |
|---|---|
| Gabapentin (Neurontin ®) | Antiepileptic |
| Lamotrigine | Antiepileptic |
| Baclofen | Antiepileptic |
| Topiramate | Antiepileptic |
| Pregabalin | Antiepileptic |
| Phenytoin (Dilatin ®) | Antiepileptic |
| Carbamazepine (Tegratol ®) | Antiepileptic |
| Valproic acid (Depakote) | Antiepileptic |
| Venlafaxine | Antidepressant |
| Paroxetine | Antidepressant |
| Amitriptyline HCl (Elavil) | Tricyclic antidepressant |
| Nortriptyline HCl (Aventyl HCl Pulvules, Pamelor) | Tricyclic antidepressant |
| Dothiepin (Dolsulepine, Prothiaden) | Tricyclic antidepressant |
| Imipramine | Tricyclic antidepressant |
| Maprotiline | Tricyclic antidepressant |
| Desipramine HCl (Norpramin) | Tricyclic antidepressant |
| Mexiletine HCl (Mexitil ®) | Antiarrhythmic |
| Tocainide (Tonocard ®) | Antiarrhythmic |
| Lidocaine HCl (Lidoderm ®) | Antiarrhythmic |
| Clomipramine | Benzodiazepine |
| Clonazepam (Klonopin) | Benzodiazepine |
| Dexamethasone (Decadron) | Corticosteroid |
| Morphine | Opioid |
| Methadone HCl (Dolophine HCl, Methadose) | Opioid |
| Fentanyl | Opioid |
| Oxycodone | Opioid |
| Tramadol HCl (Ultram) | Mixed weak opioid and serotonin reuptake blocker |
| Zostrix ® and Zostrix-HP ® | Capsaicinoid |

IV. Pharmaceutical Compositions

A host, including a human, exhibiting symptoms of a neuropathic disorder or neuropathic pain, can be treated by administering to the patient an effective amount of the active compound or a pharmaceutically acceptable prodrug or salt thereof optionally in the presence of a pharmaceutically acceptable carrier or diluent. The active materials can be administered by any appropriate route, for example, orally, parenterally, intravenously, intradermally, subcutaneously, or topically, in liquid or solid form. Nonlimiting examples include oral dosage forms, in both immediate release and extended-release or controlled release formulations, transdermal drug delivery as either a patch, gel, or cream, injection for intravenous, intraarterial, subcutaneous, epidural, intrathecal, or peripheral nerve, rectal suppository, and intranasal or inhalation therapy. The drug can be in the form of IR or ER liquid, oral solution or suspension, immediate release or controlled release tablets, pills or capsules.

A preferred dose of the compound for a neuropathic disorder will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable salts and prodrugs can be calculated based on the weight of the parent compound to be delivered. If the salt or prodrug exhibits activity in itself, the effective dosage can be estimated as above using the weight of the salt or prodrug, or by other means known to those skilled in the art.

The compound is conveniently administered in any suitable dosage form, including, but not limited to one containing 7 to 3000 mg, preferably 70 to 1400 mg of active ingredient per unit dosage form. An oral dosage of 50–1000 mg is usually convenient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition. Oral dosage forms include IR and ER liquids.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, solution, suspension, syrup, wafer, chewing gum or the like. A syrup may contain, in addition to the active compounds, sucrose as a sweetening agent and certain preservatives, dyes and colorings and flavors. Oral dosage forms include IR and ER liquids.

The compound or a pharmaceutically acceptable prodrug or salts thereof can also be mixed with other active materials that do not impair the desired action, or with materials that supplement the desired action, such as antibiotics, antifungals, anti-inflammatories, antivirals, antiepileptics, antidepressants, including tricyclic antidepressants, antiarrhythmics, benzodiazepines, corticosteroids, opioids, serotonin reuptake blockers/inhibitors, and/or capsaicinoids. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation.

Liposomal suspensions (including liposomes targeted to particular cells, for example with monoclonal antibodies) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. Usually, a daily dosage of active ingredient can be about 0.001 to 50 milligrams per kilogram of body weight. Ordinarily, a total of 0.01 to 20, preferably 0.1 to 10, milligrams per day per kilogram of body weight, given in divided doses 2 to 4 times a day or in sustained release form, is effective to obtain the desired therapeutic results.

Dosage forms (compositions) suitable for internal administration can contain about 0.25 to about 400 milligrams of active ingredient per unit. In such pharmaceutical compositions the active ingredient will ordinarily be present in a mount of about 0.01–90% by weight, based on the total weight of the composition.

The active compound can also be administered parenterally in sterile liquid dosage forms or rectally in the form of suppositories, or as a transdermal, transmucosal or intranasal formulation.

Gelatin capsules can contain the active ingredient and suitable carriers, such as lactose, sucrose, mannitol, starch, cellulose derivatives, magnesium stearate and steric acid. Similar diluents can be used to make compressed tablets. Both tablets and capsules can be manufactured as sustained release of medication over a period of hours. Compressed tablets can be sugar coated or film coated to mask any unpleasant taste and protect the tablet from the atmosphere, or they can be enteric coated for selective disintegration in the gastrointestinal tract.

Liquid dosage forms for oral administration can contain coloring and flavoring to increase patient acceptance.

In general, water, a suitable oil, saline, aqueous dextrose (glucose) and related sugar solutions and glycols, such as propylene glycol or the polyethylene glycols, are suitable carriers for parenteral solutions. Solutions for parenteral administration contain preferably a water-soluble salt of the active ingredient, suitable stabilizing agents, such as sodium bisulfite, sodium sulfite and ascorbic acid, either alone or combined, are suitable stabilizing agents. Also used are citric acid and its salts and sodium EDTA (ethylenediaminetetraacetic acid). In addition, parenteral solutions can contain preservatives, such as benzalkonium chloride, methyl- or propylparaben and chlorobutanol.

Suppositories can contain the active ingredient in a suitable oleaginous or water-soluble base. The oleaginous class includes cocoa butter and other fats with similar properties; the water-soluble class includes the polyethylene glycols.

Suitable pharmaceutical carriers are described by E. W. Martin in Remington's Pharmaceutical Sciences, a standard reference text in this field.

Some non-limiting examples of useful pharmaceutical dosage forms for administration of the compounds of this invention are listed below.

Capsules (Hard)

Hard capsules can be prepared by filling standard two-piece hard gelatin capsules with the following mixture using conventional encapsulating equipment:

Active ingredient: 1 mg

Lactose: 125 mg

Talc: 12 mg

Magnesium stearate: 3 mg

Capsules (Soft)

A mixture of active ingredient in soybean oil can be prepared and injected by means of a positive displacement pump in gelatin to form soft gelatin capsules containing 5 mg of the active ingredient. The capsules can be washed in petroleum ether and dried.

Tablets

Tablets can be prepared by conventional procedures so that each unit will contain:

Active ingredient: 1 mg

Spray dried lactose: 150 mg

Microcrystalline cellulose: 35 mg

Magnesium stearate: 3 mg

Parenteral

Parenteral composition suitable for intramuscular administration can be prepared so that each mL contains, percentages being by weight:

Active ingredient: 1 mg

Sodium carboxymethyl cellulose: 0.75%

Polysorbate 80: 0.04%

Benzyl alcohol: 0.9%

Sodium chloride: 0.9%

Water for injection Q.S.: 1 mL

Suspension

An aqueous suspension can be prepared for oral administration so that each 5 mL contain, percentages being by weight:

Active ingredient: 5 mg

Methylcellulose: 5%

Carboxymethyl cellulose: 5%

Syrup: 30%

Polysorbate 80: 0.2%

Sodium saccharin: 2 mg

Cherry flavor: 0.1%

Sodium benzoate: 5 mg
Water Q.S.: 5 mL

V. Preparation of Active Compounds

The active compound can be prepared by the using ketones $R^5C(O)R^6$ to give the tertiary carbinols as described in U.S. Pat. No. 4,485,109, or by using aldehydes $R^5CHO$ to give the secondary carbinols as described in U.S. Pat. Nos. 5,086,063 and 5,019,650.

The acetonitrile 1 (referring to FIG. 3 or 4) can be purchased or made by any means known in the art. If a piperidinethienylcarbinol is desired, the acetonitrile is difficult to source, and some routes to synthesize the acetonitrile contains highly toxic (lachrimotor) intermediates. Therefore, in a preferred embodiment, the necessary acetonitrile 1 to obtain the piperidinethienylcarbinol is synthesized from thiophene carboxaldehyde. Thiophene carboxaldehyde can be reacted with an isocyanide, preferably tosylmethyl isocyanide (TosMIC), in the presence of a base, such as potassium t-butoxide, in a protic solvent to obtain the desired acetonitrile 1.

Subsequently, the acetonitrile 1 is coupled with a bis-(2-chloroethyl) alkylamine 2 (m=2) in the presence of a base by methods described in the literature gives a 4-piperidinecarbonitrile 3 (m=2). The reaction can be carried out with sodium or potassium hydroxide in aqueous phase in the presence of a phase-transfer catalyst such as a quaternary ammonium or phosphonium salt; alternatively, bases such as sodium or potassium hydride, or sodium amide in an aprotic solvent, such as dimethyl formamide (DMF), dimethyl sulfoxide (DMSO), or tetrahydrofuran (THF) can be used. Preferred temperatures are in the range of 25° to 150° C. In a preferred embodiment, the coupling is achieved using potassium hydroxide in DMSO to minimize formation of unwanted gaseous side products (as in the case of NMP, resulting in massive heat evolution and hydrogen gas formation). In addition, a mild work-up procedure is preferred to prevent decomposition of the desired piperidinecarbonitrile 3.

The piperidinecarbonitrile 3 is then reacted with an alkylmagnesium halide (such as alkylmagnesium chloride, a Grignard reagent) in an aromatic hydrocarbon solvent, preferably at a temperature in the range of 25°–150° C., or with an alkyllithium reagent in a mixture of ethyl ether and an aromatic or aliphatic hydrocarbon solvent at a temperature in the range of –50° to 100° C. In a preferred embodiment of the present invention, the piperidinecarbonitrile 3 is reacted with a alkylmagnesium bromide rather than alkylmagnesium chloride to obtain a more complete conversion. Subsequent quenching with water gives the imine 4 which can then be hydrolyzed with an aqueous inorganic acid, such as hydrochloric or sulfuric acid, to give the ketone 5. Imine 4 carrying an $R^4$ group having substituents in the ortho portion, usually need to be heated to 50°–100° C. to effect the hydrolysis; others hydrolyze at room temperature. The conversion of 3 to 5 via 4 is also a well-known method in the literature.

Reduction of a ketone 5 to a secondary alcohol ($R^6$ is hydrogen) is best effected by sodium borohydride in ethanol or lithium borohydride in an ether solvent such as tetrahydrofuran at a temperature in the range of –20° to 50° C. Other hydride reducing agents, such as lithium aluminum hydride can also be used.

Treatment of a ketone 5 with alkyllithium reagents or alkylmagnesium halide reagents gives the tertiary carbinol 6 ($R^6$ is alkyl). In a preferred embodiment, the ketone 5 is treated with alkyllithium with the use of some polar additives to promote further conversion of ketone 5 into the tertiary carbinol 6. Alternatively, the transformation can be carried out with alkyl cerium species obtained from anhydrous cerium chloride and alkyllithium reagents and described by T. Imamoto et al., Tetrahedron Lett., 25, 4233(1984). These reagents may give higher yields and fewer side reactions. The reactions can be carried out in ether solvents such as tetrahydrofuran, preferably at a temperature in the range of –100° to 50° C. The tertiary carbinol can also be prepared by reaction of the cerium species with an ester derivative of ketone 5, which can be prepared from a piperidinecarbonitrile 3 by methods described in the literature, such as hydrolysis with sulfuric acid followed by esterification.

Pyrrolidinecarbinols (m=1) and hexahydroazepinecarbinols (m=3) are prepared analogously from the necessary bis-chloro alkylamine to obtain the corresponding intermediate nitrile and ester, which can be further derivatized to obtain the carbinol. The esters are prepared by methods described in the literature.

Variation of $R^1$: compounds of Formula (I) or (II) with various groups $R^1$ can be prepared starting from the corresponding amines 2. Alternatively, a methyl group $R^1$ can be replaced by other groups as follows:

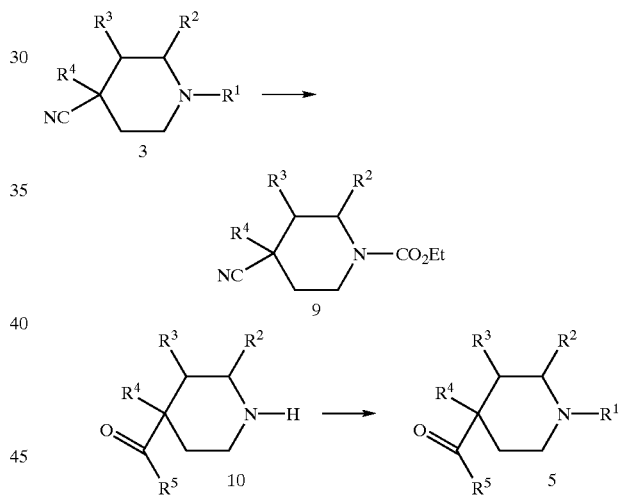

Nitriles 3, on heating with alkyl chloroformates in a hydrocarbon solvent such as benzene or toluene at a temperature in the range of 50°–150° C. give the urethanes 9. The latter, on reaction with a Grignard reagent in a hydrocarbon solvent such as benzene or toluene, give a ketones 10 where $R^1$ is hydrogen. This ketone is converted into a ketones 5 with an alkyl or allyl halide $R^1X$ (where X is halo, and preferably Cl, Br or I) in a solvent such as dimethylformamide or tetrahydrofuran, at a temperature in the range of 0°–100° C. in the presence of a base such as sodium or potassium carbonate.

Alternatively, ketone of Formula 10 can also be obtained by treating a ketone 5 (where $R^1$ is methyl) with alkyl chloroformates as described above to give a urethane of Formula 11. This compound, on hydrolysis with an aqueous acid, such as hydrochloric or sulfuric acid, at a temperature of 50°–100° C., gives a ketone of Formula 10.

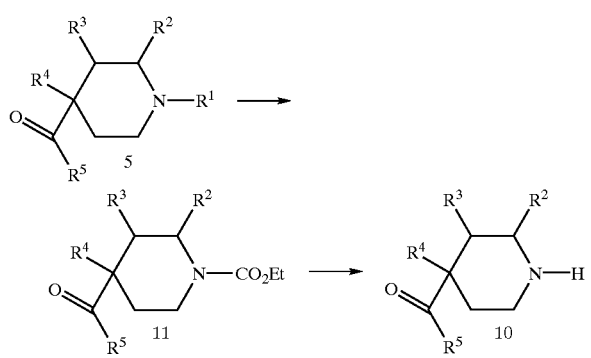

For secondary carbinols (where $R^6$ is hydrogen) having groups $R^1$ as $CH_2R^9$ the following methods can also be used.

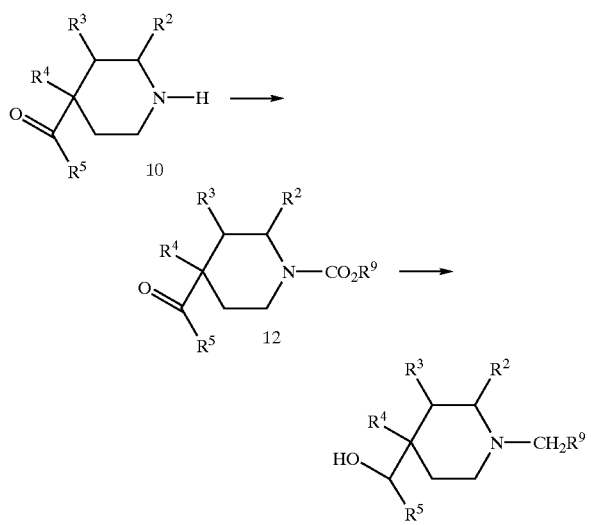

$R^9$ is either methyl or ethyl, which on reduction of 12 gives compounds of Formula I where $R^1$ is ethyl or n-propyl respectively.

Ketones 10, on treatment with an acyl chloride $R^9COX$ (where X is halo, and preferably chloro) or an anhydride $R^9C(O)OC(O)R^9$ in the presence of a base, such as sodium or potassium hydroxide in aqueous solution, or pyridine in an aprotic solvent such as methylene chloride, at temperatures of −30° to 50° C., give the amides 12 which on reduction with borane or complex hydrides such as lithium aluminum hydride give the secondary carbinols. This method is exemplified by Example 2.

Esters of compounds of formula (I) ($R^1$ is alkanoyl) are prepared by treatment of compounds of formula (I) ($R^1$ is hydrogen) with a suitable anhydride, or an acid chloride in the presence of a base such as pyridine, preferably at temperatures of 0°–150° C.

Ethers of compounds of formula (I) ($R^1$ is alkyl) are prepared by treatment of compounds of formula (I) ($R^1$ is hydrogen) with a base, such as sodium or potassium hydride, or sodium amide, in an aprotic solvent such as tetrahydrofuran or dimethylformamide, preferably at a temperature in the range of 0°–100° C., followed by addition of a alkylhalide $R^1X$ (wherein X is a halogen, preferably Cl, Br or I), preferably at temperatures of 0°–100° C. Any quaternary ammonium salts of compounds of formula (I) formed are then converted into the tertiary bases by treatment with potassium methylmercaptide in an aprotic solvent such as dimethylformamide, preferably at a temperature in the range of 50°–150° C. Alternatively, such ethers can be prepared by reaction of compounds of formula (I) ($R^1$ is hydrogen) with diazoalkanes $R^1N_2$ (wherein $R^1$ is a methylene radical) in the presence of a catalyst such as a rhodium complex.

Suitable salts formed with pharmaceutically acceptable acids, such as hydrochloric, sulfuric, phosphoric and maleic acids, can also be prepared. Such salts are usually preferable when the free bases are oils. Such salts may also be more stable to storage, and may be better absorbed orally, than the free bases. In a preferred embodiment, the compound of the present invention is in the form of its hydrochloride salt.

The present invention is described by way of illustration, in the following examples. It will be understood by one of ordinary skill in the art that these examples are in no way limiting and that variations of detail can be made without departing from the spirit and scope of the present invention.

EXAMPLES

All reagents were used as received unless stated otherwise. Anhydrous solvents were purchased from Aldrich Chemical Company, Inc. (Milwaukee). Melting points (mp) were determined on an Electrothermal digit melting point apparatus and are uncorrected. $^1H$ and $^{13}C$ NMR spectra were taken on a Varian Unity Plus 400 spectrometer at room temperature and reported in ppm downfield from internal tetramethylsilane. Deuterium exchange, decoupling experiments or 2D-COSY were performed in order to confirm proton assignments. Signal multiplicities are represented by s (singlet), d (doublet), dd (doublet of doublets), t (triplet), q (quadruplet), br (broad), bs (broad singlet), m (multiplet). All J-values are in Hz. Mass spectra were recorded on a JEOL JMS-SX/SX102A/E mass spectrometer. Analytic TLC was performed on Whatman LK6F silica gel plates, and preparative TLC on Whatman PK5F silica gel plates. Column chromatography was carried out on Silica Gel (Fisher, S733-1) at atmospheric pressure.

Example 1

4-(3'-Chlorophenyl)-α,1-dimethyl-4-piperidinemethanol (m=2; $R^1,R^5$=Me; $R^2$, $R^3,R^6,R^7$=H; $R^4$=3-$ClC_6H_4$)

Sodium borohydride (3.5 g, 92 mmoles) was added slowly to a cooled mixture of 23.9 g (95 mmoles) of 1-[4-(3'-chlorophenyl)-1-methyl-4-piperidinyl]ethanone and 100 mL of ethanol. Water was added after stirring at room temperature for 2 hours, and the mixture was extracted with methylene chloride to give 24.1 g of crude product. A sample crystallized from ethyl acetate had m.p. 125°–126° C., $^1H$ NMR (CDCl$_3$): δ 7.2–7.4 (m,4H); 3.6 (quartet, J=7 Hz,1H); 2.8 (m,2H); 1.5–2.5 (m,10H) and 1.0 (d, J=7 Hz,3H).

The hydrochloride had m.p. 202° C.–205° C. after crystallization from isopropyl alcohol. Anal. Calcd. for $C_{14}H_{21}Cl_2NO$: C, 57.93; H, 7.29; N, 4.83. Found: C, 57.92; H, 7.14; N, 5.11.

The starting material, 1-[4-(3'-chlorophenyl)-1-methyl-4-piperidinyl]-ethanone was obtained by either of the two following methods:

(a) To 400 mL of toluene was added 117 mL (0.35 mole) of 3M methylmagnesium chloride in tetrahydrofuran. Using a Vigreux column, 300 mL of solvent were then distilled off during 1 hour. To the cooled residue was added 47 g (0.20 mole) of 4-(3'-chlorophenyl)-1-methylpiperidine-4-carbonitrile, and the mixture was heated under reflux for 2 hours. Ten percent hydrochloric acid (400 mL) was added to the mixture, keeping the temperature below 25° C. The layers were separated after stirring at room temperature for 6 hours, and the toluene was extracted with 50 mL of water. The combined water layers were made strongly basic with conc. ammonium hydroxide solution. Extraction with methylene chloride, removal of the solvent from the dried extracts, and rapid short-path distillation of the residue (160° C. bath temperature, 0.1 mm) gave 44.2 g (88% yield) of 1-[4-(3'-chlorophenyl)-1-methyl-4-piperidinyl]-ethanone as an oil that rapidly crystallizes. $^1$H NMR (CDCl$_3$): δ 7.2–7.4 (m,4H); 2.7 (m,2H); 2.5 (m,2H); 2.3 (s,3H); 2.0–2.3 (m,4H) and 2.0 (s,3H), IR (neat) 1708 cm$^{-1}$.

(b) To 12.37 g (52 mmoles) of 4-(3-chlorophenyl)-1-methylpiperidine-4-carbonitrile dissolved in 75 mL of toluene was added 75 mL of 1.4M methyl lithium in ether (105 mmoles), keeping the temperature below 0° C. The mixture was stirred at 0° C. for 30 minutes and at 25° C. for 3 hours. Ten percent hydrochloric acid (100 mL) was added and the mixture was stirred at room temperature for 3 hours. The layers were separated, and the toluene/ether layer was extracted with 20 mL of water. The combined aqueous phases were made strongly basic with aqueous sodium hydroxide and the mixture was extracted with methylene chloride. Removal of the solvent from the dried solution gave 12.7 g of crude 1-[4-(3'-chlorophenyl)-1-methyl-4-piperidinyl]-ethanone, identical by NMR and IR spectroscopy with the product prepared according to procedure (a).

The starting material, 4-(3-chlorophenyl)-1-methylpiperidine-4-carbonitrile was prepared as follows by the procedure of T. Cammack and P. C. Reeves, J. Heterocycl. Chem., 23, 73 (1986): a mixture of 100 g (0.52 mole) of N,N-bis(chloroethyl)methylamine hydrochloride, 80 g (0.53 mole) of 3-chlorobenzyl cyanide, 13 g of hexadecyltributyl-phosphonium bromide and 750 mL of 50% aqueous sodium hydroxide was stirred at 100° C. internal temperature for 1 hour. Water (750 mL) was added to the cooled mixture that was then extracted with 500 mL and three 100-mL portions of toluene. Removal of the solvent from the dried/solution and rapid short-path distillation of the residue (160° C. bath temperature, 0.1 mm) gave 107.2 g (88% yield) of 4-(3-chlorophenyl)-1-methylpiperidine-4-carbonitrile as a colorless oil which slowly crystallizes. $^1$H NMR (CDCl$_3$): δ 7.5 (s,1H); 2.3 (m,3H); 3.0 (d,2H); 2.5 (m,2H); 2.4 (s,3H) and 2.1 (m,4H). The hydrochloride had m.p 235° C.–236° C. after crystallization from isopropyl alcohol.

Example 1a 4-(3'-Chlorophenyl)-α,α,1-trimethyl-4-piperidinemethanol (m=2; R$^1$,R$^5$; R$^6$=Me; R$^2$,R$^3$,R$^6$,R$^7$=H; R$^4$=3-ClC$_6$H$_4$)

This compound was made by a modification of the general method described by T. Imamoto, Y. Sagiura, and N. Takiyama, Tetrahedron Lett., 25, 4233 (1984) for the addition of organocerium reagents to ketones: cerium chloride heptahydrate (3.39 g, 9.1 mmoles) was dried at 140° C./0.1 mm for 2 hours. Tetrahydrofuran (20 mL) was added with ice cooling, and the mixture was stirred under nitrogen for 2 hours. Methyl lithium (6.5 mL of a 1.4 M solution in ether, 9.1 mmoles) was added at −70° C., and the mixture was stirred at −70° C. for 30 minutes. A solution of 0.72 g (2.7 mmoles) of 1-[4-(3'-chlorophenyl)-1-methyl-4-piperidinyl]-ethanone (Example 1) in 2 mL of tetrahydrofuran was added at −70° C., and the mixture was allowed to come to room temperature. Methylene chloride and aqueous ammonium hydroxide solution were added, keeping the temperature below 0° C. The mixture was filtered, and the solids were washed repeatedly with methylene chloride. The layers in the combined filtrate were separated and the methylene chloride layer was dried. Removal of the solvent gave 0.76 g of the title compound, identical by NMR and IR spectroscopy with the product obtained by the procedure described in U.S. Pat. No. 4,485,109. The hydrochloride had m.p. 276° C. (dec.) after crystallization from ethanol. Anal. Calcd. for C$_{15}$H$_{23}$Cl$_2$NO: C, 59.21; H, 7.62; N, 4.60. Found: C, 59.08; H, 7.70; N, 4.37.

4-(3'-Chlorophenyl)-α,α,1-trimethyl-4-piperidinemethanol was also prepared using the above procedure but starting with ethyl 4-(3-chlorophenyl)-1-methylpiperidine-4-carboxylate. The latter was prepared as follows by the procedure of J. Diamond, W. F. Bruce, and F. T. Tyson, J. Org. Chem., 22, 399 (1957): 4-(3-chlorophenyl)-1-methylpiperidine-4-carbonitrile (Example 1) was added to 15 mL of 80% of sulfuric acid and the mixture was stirred in an 125° C. oil bath for 4 hours. Ethanol (60 mL) was added with cooling, and the mixture was heated under reflux for 16 hours and then poured onto ice. The aqueous mixture was extracted with methylene chloride and the extracts were washed with aqueous sodium carbonate. Removal of the solvent from the dried methylene chloride solution and short-path distillation of the residue (180° C. bath, 1 micron) gave 9.23 g (67%) of ethyl 4-(3-chlorophenyl)-1-methylpiperidinecarboxylate. $^1$H NMR (CDCl$_3$): δ 7.4 (s,1H); 7.3 (m,3H); 4.1 (quartet, J=7 Hz,2H); 2.8 (d,2H); 2.6 (d,2H); 2.3 (s,3); 2.2 (t,2H); 2.0 (t,2H) and 1.2 (t, J=7 Hz,3H).

Example 2

4-(3'-Chlorophenyl)-1-ethyl-α-methyl-4-piperidinemethanol (m=2; R$^1$=Et; R$^4$=3-ClCH$_6$H$_4$; R$^5$=Me; R$^2$,R$^3$,R$^6$,R$^7$=H)

Ethyl chloroformate (6.5 g) was added to a solution of 5.0 g of 1-[4-(3'-chlorophenyl)-1-methyl-4-piperidinyl]-ethanone (Example 1) in 25 mL of benzene. The mixture was heated under reflux for 3 hours, cooled, and filtered. The filtrate was washed with 10% aqueous sodium carbonate, dried and concentrated to give 5.71 g of ethyl 4-acetyl-4-(3'-chlorophenyl)-1-piperidine carboxylate (11; R$^2$,R$^3$=H; R$^4$=3-ClC$_6$H$_4$).

A mixture of 4.69 g of the above product, 25 mL of conc. hydrochloric acid, and 10 mL of water was heated under reflux for 18 hours. The cooled mixture was made basic with 15% aqueous sodium hydroxide solution and extracted with methylene chloride to give 3.35 g of 1-[4-(3'-chlorophenyl)-4-piperidinyl]ethanone (10,R$^1$,R$^2$,R$^3$=H; R$^4$=3-ClC$_6$H$_4$). The hydrochloride had m.p. 254° C. (dec.). Anal. Calcd. for C$_{13}$H$_{17}$Cl$_2$NO; C, 56.94; H, 6.25; N, 5.11. Found: C, 56.89; H, 6.38; N, 5.51.

To a mixture of 1.0 g of the above free base, 10 mL of methylene chloride and 20 mL of 15% aqueous sodium hydroxide was added with cooling 1 mL of acetyl chloride and the mixture was stirred at room temperature for 1 hour. The aqueous phase was extracted with methylene chloride, and the combined organic phases were dried and concentrated to give 1.15 g of 1,4-diacetyl-4-(3'-chlorophenyl)-1-piperidine (12,R$^2$,R$^3$=H; R$^{4=3}$-ClC$_6$H$_4$; R$^5$,R$^9$=Me).

The above amide was dissolved in 10 mL of dry tetrahydrofuran, and 1 mL of borane methyl sulfide complex was added. The mixture was heated under reflux for 6 hours, cooled, and treated with 5 mL of conc. hydrochloric acid. The solvents were removed under vacuum, and the residue was heated with 20 mL of 10% hydrochloric acid in an 100° C. oil bath for 2 hours. The cooled mixture was made basic with aqueous sodium hydroxide and extracted with methylene chloride to give 0.90 g of the crude title compound. It was purified by short-path distillation (to 200° C. bath temperature, 1 micron) followed by crystallization from ethyl acetate. M.p. 89° C.–94° C.; $^1$H NMR (CDCl$_3$): δ 7.2–7.4 (m,4H); 3.7 (quartet, J=7 Hz,1H); 2.8 (d,2H); 1.2–2.5 (m,9H); 1.0 (t, J=7 Hz,3H) and 0.9 (d, J=7 Hz,3H). Anal. Calcd. for C$_{15}$H$_{22}$ClNO: C, 67.27; H, 8.28; N, 5.23. Found: C, 67.18; H, 8.14; N, 5.21.

Table 1 is illustrative of the novel aryl piperidinecarbinols that were prepared or could be prepared by the methods listed hereinabove but is not meant to be limiting in breadth.

TABLE 2

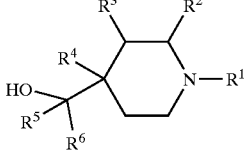

| $R^1$ | $R^2$ | $R^3$ | $R^4$ | $R^5$ | $R^6$ | MP (° C.) |
|---|---|---|---|---|---|---|
| Me | H | H | 3-ClC$_6$H$_4$ | Me | H | 202–205* |
| Me | H | H | 3-ClC$_6$H$_4$ | Me | Me | 278(dec)* |
| Et | H | H | 3-ClC$_6$H$_4$ | Me | H | 89–94 |
| Me | H | H | C$_6$H$_5$ | Me | H | 119–120 |
| Me | H | H | 2-FC$_6$H$_4$ | Me | H | 181–184(dec)** |
| Me | H | H | 3-FC$_6$H$_4$ | Me | H | 127–128 |
| Me | H | H | 4-FC$_6$H$_4$ | Me | H | 142–143 |
| Me | H | H | 3,4-F$_2$C$_6$H$_3$ | Me | H | 135–136 |
| Me | H | H | 4-ClC$_6$H$_4$ | Me | H | 171–172 |
| Me | H | H | 3,4-Cl$_2$C$_6$H$_3$ | Me | H | 175–177 |
| Me | H | H | 3-BrC$_6$H$_4$ | Me | H | 179(dec)** |
| Me | H | H | 4-BrC$_6$H$_4$ | Me | H | 186 |
| Me | H | H | 2-MeC$_6$H$_4$ | Me | H | 102–106 |
| Me | H | H | 3-MeC$_6$H$_4$ | Me | H | 97–99 |
| Me | H | H | 4-MeC$_6$H$_4$ | Me | H | 161–163(dec)** |
| Me | H | H | 3-CF$_3$C$_6$H$_4$ | Me | H | 111–112 |
| Me | H | H | 4-CF$_3$C$_6$H$_4$ | Me | H | 188–189 |
| Me | H | H | 4-MeOC$_6$H$_4$ | Me | H | 114–115 |
| Me | H | H | 3-Me$_2$NC$_6$H$_4$ | Me | H |  |
| Me | H | H | 3-MeSC$_6$H$_4$ | Me | H |  |
| Me | H | H | 3,5-Cl$_2$C$_6$H$_3$ | Me | H |  |
| Me | H | H | 3-CF$_3$C$_6$H$_4$ | Me | H |  |
| Me | H | H | 3-C$_6$H$_5$OC$_6$H$_4$ | Me | H |  |
| Me | H | H | 3-C$_6$H$_{13}$C$_6$H$_4$ | Me | H |  |
| Me | H | H | 2-C$_3$H$_7$SC$_6$H$_4$ | Me | H |  |
| Me | H | H | 2-naphthyl | Me | H | 191–192 |
| Me | H | H | 2-thienyl | Me | H | 104–105 |
| Me | H | H | 3-thienyl | Me | H | 126–127 |
| Me | H | H | 2-benzothienyl | Me | H |  |
| Me | H | H | 3-benzothienyl | Me | H | 184–188(dec)** |
| Me | H | H | 2-benzofuryl | Me | H |  |
| Me | H | H | 3-benzofuryl | Me | H |  |
| Me | H | H | 2-pyridyl | Me | H |  |
| Me | H | H | 3-pyrrolyl | Me | H |  |
| n-Pr | H | H | 3-ClC$_6$H$_7$ | Me | H | 108–110 |
| Me | H | H | 3-ClC$_6$H$_4$ | Et | H | 123.5–125 |
| Me | H | H | 3-ClC$_6$H$_4$ | -n-Pr | H | 150–153** |
| Me | H | H | 3-ClC$_6$H$_4$ | -n-Bu | H | 95–96 |
| allyl | Me | H | 3-ClC$_6$H$_4$ | Me | H |  |
| Me | (CH$_2$)$_4$ |  | 3-ClC$_6$H$_4$ | Et | H |  |
| Et | H | Me | 3-ClC$_6$H$_4$ | -n-Bu | H |  |
| Me | H | H | 3-BrC$_6$H$_4$ | Me | Me | 285(dec)* |
| allyl | H | H | 3-ClC$_6$H$_4$ | Me | Me | 131–132** |
| Me | H | H | 2-thienyl | Me | Me | 133–134 |
| Me | H | H | 3-thienyl | Me | Me | 157–158 |
| Me | H | H | 3-benzothienyl | Me | Me | 134–135 |
| Me | H | H | 2-pyridyl | Me | Me | 91–92 |
| Me | H | H | 2-benzothienyl | Me | Me |  |
| Me | H | H | 3-benzofuryl | Me | Me |  |
| Me | H | H | 3-(1'-methyl-pyrrolyl) | Me | Me |  |
| Me | H | H | 1-naphthyl | Me | Me | 131–132 |
| Me | H | H | 3-(5'-chloro-thienyl) | Me | Me |  |
| Me | n-Bu | m-Pr | 3-ClC$_6$H$_4$ | Me | H |  |
| (CH$_2$)$_3$ |  | H | 3-ClC$_6$H$_4$ | Me | H |  |
| Me | (CH$_2$)$_6$ |  | 3-ClC$_6$H$_4$ | Me | H |  |
| Me | H | H | 3-(n-C$_{10}$H$_{22}$)—C$_6$H$_4$ | Me | H |  |
| Me | H | H | 3-C$_6$H$_5$-5-ClC$_6$H$_3$ | Me | H |  |
| Me | H | H | 3-C$_6$H$_5$C$_6$H$_3$Cl-5 | Me | H |  |
| Me | H | H | 3-(3'-ClC$_6$H$_4$)—C$_6$H$_4$ | Me | H |  |
| Me | H | H | 3-Cl-1-naphthyl | Me | H |  |
| Me | H | H | 2-(3-CH$_3$-thienyl) | Me | H |  |
| Me | H | H | 2-(5-Cl-benzo-thienyl) | Me | H |  |

TABLE 2-continued

| R¹ | R² | R³ | R⁴ | R⁵ | R⁶ | MP (° C.) |
|---|---|---|---|---|---|---|
| Me | H | H | 2-(5-Cl-benzo-furyl) | Me | H | |
| Me | H | H | 3-(5-Cl-benzo-furyl) | Me | H | |
| Me | H | H | 3-BrC₆H₄ | (CH₂)₃ | | |
| Me | H | H | 3-BrC₆H₄ | (CH₂)₆ | | |

*hydrochloride salt
**fumarate salt

Example 3
4-(3'-Chlorophenyl)-α,1-dimethyl-4-piperidinemethanol Acetate (m=2; $R^1,R^5$=Me; $R^4$=3-ClC₆H₄; $R^2,R^3,R^6$=H, $R^7$=CH₃CO)

A mixture of 1.00 g of 4-(3'-chlorophenyl)-α,1-dimethyl-4-piperidinemethanol (Example 1) and 5 mL of acetic anhydride was heated under reflux for 90 minutes. Removal of the excess acetic anhydride and short-path distillation of the residue (170° C. bath temperature, 1 micron) gave 1.05 g of the title compound as an oil. ¹H NMR (CDCl₃): δ 7.1–7.4 (m, 4H); 4.9 (quartet, J=7 Hz,1H); 2.8 (m,2H); 2.2 (s,3H); 2.0 (s,3H); 1.9–2.4 (m,6H); and 0.9 (d,J=7 Hz,3H).

The salt with fumaric acid had m.p. 194° C. (dec.) after crystallization from isopropyl alcohol. Anal. Calcd. for C₂₀H₂₆ClNO₆; C, 58.23; H, 6.36. Found: C, 58.32; H, 6.41.

Example 4
4-(3'-Chlorophenyl)-α,α,1-trimethyl-4-piperidinemethanol Acetate (m=2; $R^1,R^5$, $R^6$=Me; $R^2,R^3$=H; $R^4$=3-ClC₆H₄; $R^7$=CH₃CO)

A mixture of 1.04 g of 4-(3'-Chlorophenyl)-α,α-1-trimethyl-4-piperidinemethanol (Example 2) and 10 mL of acetic anhydride was heated under reflux for 2 hours. Removal of the excess acetic anhydride followed by short-path distillation of the residue (170° C. bath temperature, 1 micron) gave 1.07 g of the title compound as an oil that slowly crystallized. ¹H NMR (CDCl₃): δ 7.3 (s,1H); 7.2 (m,3H); 2.7 (d,2H); 2.2 (s,3H), 2.0 (s,3H); 1.8–2.5 (m,6H) and 1.4 (s,6H). High-resolution mass spectrum m/e calcd. for C₁₇H₂₄ClNO₂; 309.1495; measured: 309.1486.

Example 5
4-(3'-Chlorophenyl)-4-(1-methoxymethyl)-1-methylpiperidine (m=2; $R^1,R^5,R^7$=Me; $R^2,R^3,R^6$=H— $R^4$=3-ClC₆H₄)

Potassium hydride oil suspension (3.80 g of 35%; 33 mmoles) was washed with hexane, 15 mL of tetrahydrofuran was added, and the suspension was treated with 4.25 g (16 mmoles) of 4-(3'-chlorophenyl)-α, 1-dimethyl-4-piperidinemethanol (Example 1) dissolved in 15 mL of tetrahydrofuran. The mixture was stirred at room temperature for 1 hour; methyl iodide (9.1 g, 64 mmoles) was added which caused the temperature to rise to 50° C. Methanol (5 mL) was added after stirring for 2.75 hours, keeping the temperature below 25° C. Water and chloroform were added, and the mixture was filtered to remove 4.70 g of the methiodide of the title compound. This solid was combined with the products obtained on removal of the solvent from the chloroform layer, and heated with 7.0 g of potassium methylmercaptide in 30 mL of dimethyl formamide in an 80° C. oil bath for 2.5 hours. The solvent was removed, water was added to the residue and the mixture was extracted with methylene chloride. Removal of the solvent from the dried extracts and short-path distillation of the residue (130° C. bath temperature, 1 micron) gave 3.94 g (88% yield) of the title compound as an oil. ¹H NMR (CDCl₃): δ 7.2–7.4 (m,4H); 3.3 (s,3H); 3.2 (quartet, J=7 Hz,1H); 2.7 (m,2H); 2.2 (s,3H); 1.8–2.4 (m,6H); and 0.9 (d,J=7 Hz,3H). High resolution mass spectrum: m/e calcd. for C₁₅H₂₂ClNO: 267.1390; measured: 267.1393.

Example 6
4-(3'-Chlorophenyl)-4-(1'-benzyloxymethyl)-1-methylpiperidine (m=2; $R^1,R^5$=Me; $R^2,R^3,R^6$=H; $R^4$=3-ClC₆H₄; $R^7$=C₆H₅CH₂)

Following the procedures above, but using benzyl bromide in place of methyl iodide, the title compound was obtained as an oil, distilling at a bath temperature of up to 210° C. at 1 micron. ¹H NMR (CDCl₃): δ 7.2–7.4 (m,9H); 3.4 (quartet, J=7 Hz,1H); 2.7 (m,2H); 2.4 (m,1H); 2.2 (s,3H); 2.0 (m,5H) and 0.9 (d,J=7 Hz,3H). High resolution mass spectrum: calcd. for C₂₁H₂₆ClNO: m/e 343.1703; measured: 343.1693.

Example 7
3-(3'-Chlorophenyl)-α,α,1-trimethyl-3-pyrrolidinemethanol (m=1; $R^1,R^5$, $R^6$=Me; $R^2,R^3,R^7$=H; $R^4$=3-ClC₆H₄)

A solution of 2.83 g of ethyl 3-(3'-chlorophenyl)-1-methyl-3-pyrrolidinecarboxylate in 5 mL of tetrahydrofuran was added to 8 mL of 3M methylmagnesium chloride in tetrahydrofuran and the mixture was heated under reflux for 4 hours. Ten percent hydrochloric acid was added and the mixture was washed with ether. The aqueous phase was made basic with ammonium hydroxide solution and extracted with methylene chloride. Removal of the solvent from the dried extract gave 1.94 g of crude title compound. It was purified by chromatography on silica (elution with 3:1 methylene chloride/methanol), followed by crystallization from acetonitrile m.p. 98°–99° C. ¹H NMR (CDCl₃): δ 7.0–7.3 (m,4H); 3.7 (d, J=7 Hz,1H); 3.2 (m,2H); 2.8 (m,1H); 2.4 (d, J=10 Hz, 1H); 2.4 (s,3H) 2.2 (m,2H); 1.2 (s,3H) and 1.1 (s,3H). High resolution mass spectrum: m/e calcd. for C₁₄H₂₀ClNO: 253.1233; measured: 253.1235.

The starting material, ethyl 3-(3'-chlorophenyl)-1-methyl-3-pyrrolidine carboxylate, was prepared from 3-chlorobenzyl cyanide by the procedure of R. L. Jacoby, K. A. Nieforth, and R. E. Willete, J. Med. Chem., 17,453 (1974). ¹H NMR (CDCl₃): δ 7.1–7.4 (m,4H); 4.1 (quartet, J=7 Hz,2H); 3,6 (d, J=8 Hz, 1H); 2.9 (m,2H); 2.7 (d, J=8 Hz, 1H); 2.0–2.5 (m+s,5H) and 1.2 (t,J=7 Hz,3H).

Example 8

4-(3 'Chlorophenyl)-α,1-dimethyl-2,3,4,5,6,7-hexahydro-1H-azepine-4-methanol (m=3; $R^1,R^5$=Me; $R^4$=3-ClC$_6$H$_4$; $R^2,R^3,R^6,R^7$=H)

Sodium borohydride (0.22 g) was added with cooling to a solution of 1.0 g of 1-[4-(3-chlorophenyl)-1-methyl-4-(2,3,4,5,6,7-hexahydro-1H-azepinyl]ethanone in 2 mL of ethanol. The mixture was stirred at room temperature for 18 hours. Water was added and the mixture was extracted repeatedly with methylene chloride. Removal of the solvent and crystallization of the residue from acetonitrile gave 0.54 g of the title compound, m.p. 123°–124° C. $^1$H NMR (CDCl$_3$): δ 7.2–7.4 (m,4H); 3.6 (quartet, J=7 Hz,1H); 2.7 (m,2H); 2.4 (m,1H); 2.2 (s,3H); 1.6–2.0 (m,8H) and 1.0 (d, J=7 Hz,3H). High-resolution mass spectrum: m/e calcd. for $C_{15}H_{22}ClNO$: 267.1390; measured: 267.1388.

The starting material, 1-[4-(3-chlorophenyl)-1-methyl-4-(2,3,4,5,6,7-hexahydro-1H-azepinyl]ethanone was prepared as described in Example 1 by the addition of methylmagnesium chloride to 4-(3'-Chlorophenyl)-α,1-dimethyl-2,3,4,5,6,7-hexahydro-1H-azepine-4-carbonitrile. The latter was prepared from 3-chlorobenzyl cyanide by the procedure of J. Diamond, W. F. Bruce and F. T. Tyson, J. Org. Chem., 399 (1957).

TABLE 3

| $R^1$ | $R^2$ | $R^3$ | $R^4$ | $R^5$ | $R^6$ | $R^7$ | m | MP (° C.) |
|---|---|---|---|---|---|---|---|---|
| Me | H | H | 3-ClC$_6$H$_4$ | Me | H | Ac | 2 | 194 (dec)** |
| Me | H | H | 3-ClC$_6$H$_4$ | Me | Me | Ac | 2 | (solid)* |
| Me | H | H | 3-ClC$_6$H$_4$ | Me | H | Me | 2 | (oil)* |
| Me | H | H | 3-ClC$_6$H$_4$ | Me | H | CH$_2$C$_6$H$_5$ | 2 | (oil)* |
| Me | H | H | 3-ClC$_6$H$_4$ | Me | Me | H | 1 | 98–99 |
| Me | H | H | 3-ClC$_6$H$_4$ | Me | H | H | 3 | 123–124 |
| Me | H | H | 3-ClC$_6$H$_4$ | Me | Me | H | 3 | |
| Me | H | H | 3-ClC$_6$H$_4$ | Me | H | H | 1 | |
| Me | H | H | 3-CF$_3$C$_6$H$_4$ | Me | Me | H | 3 | |
| Me | H | H | 3-CF$_3$C$_6$H$_4$ | Me | H | H | 1 | |
| Me | H | H | 3-ClC$_6$H$_4$ | Me | Me | Me | 1 | |
| Et | Me | H | 3-thienyl | Me | Me | H | 3 | |
| n-Pr | H | Me | 2-bromothienyl | Me | Et | H | 3 | |
| Me | H | H | 3-BrC$_6$H$_4$ | Me | Me | H | 1 | |
| Me | H | H | 3-BrC$_6$H$_4$ | Me | Me | H | 3 | |
| Me | H | H | 3-ClC$_6$H$_4$ | Me | H | Ac | 3 | |
| Me | H | H | 2-thienyl | Me | H | H | 1 | |
| Me | H | H | 2-thienyl | Me | Me | H | 3 | |
| Me | H | H | 3-ClC$_6$H$_4$ | Me | H | n-butyl | 2 | |
| Me | H | H | 3-ClC$_6$H$_4$ | Me | Me | CO-n-butyl | 2 | |

*for NMR and HRMS data, see experimental procedure
**Fumarate salt

Example 9

Synthesis of the Acetonitrile (1)

The acetonitrile 1 of the present invention is synthesized from thiophene carboxaldehyde. Thiophene carboxaldehyde can be reacted with tosylmethyl isocyanide (TosMIC), in the presence of potassium t-butoxide, in a solution of 1,2-dimethoxyethane (DME) and ethanol to obtain the desired acetonitrile 1.

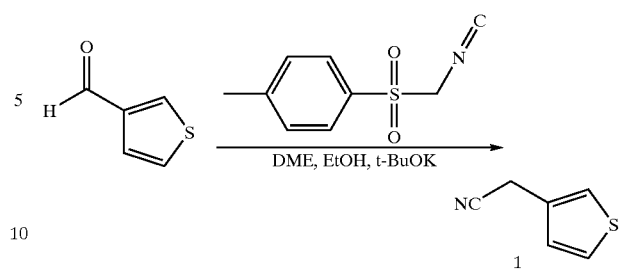

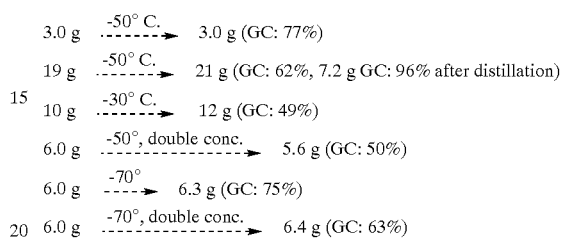

| | | |
|---|---|---|
| 3.0 g | -50° C. → | 3.0 g (GC: 77%) |
| 19 g | -50° C. → | 21 g (GC: 62%, 7.2 g GC: 96% after distillation) |
| 10 g | -30° C. → | 12 g (GC: 49%) |
| 6.0 g | -50°, double conc. → | 5.6 g (GC: 50%) |
| 6.0 g | -70° → | 6.3 g (GC: 75%) |
| 6.0 g | -70°, double conc. → | 6.4 g (GC: 63%) |

Example 10

Synthesis of the Piperidinecarbonitrile (3)

The acetonitrile 1 is coupled with a bis-(2-chloroethyl) methylamine 2 in the presence of potassium hydroxide in DMSO at 18–20° C. to obtain 3.

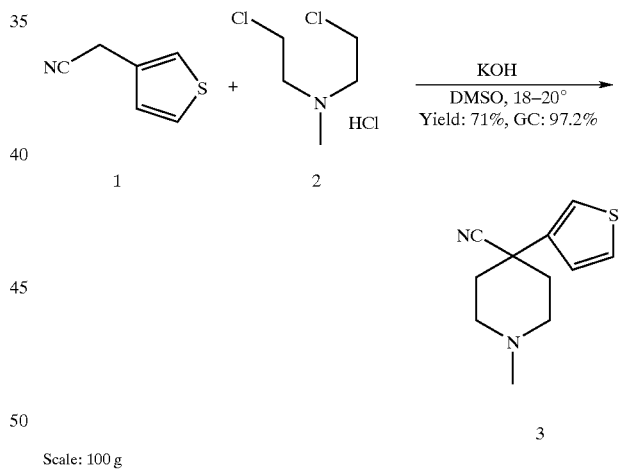

Scale: 100 g

Example 11

Synthesis of the Ketone (5)

The piperidinecarbonitrile 3 is then reacted with a methylmagnesium bromide in THF, at 80° C. After the reaction went to completion, the reaction mixture was quenching with water to give the imine, which was then hydrolyzed with an aqueous hydrochloric acid, to give the a ketone 5.

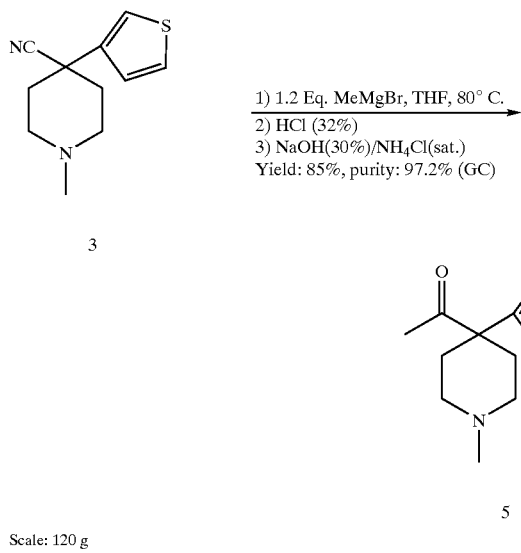

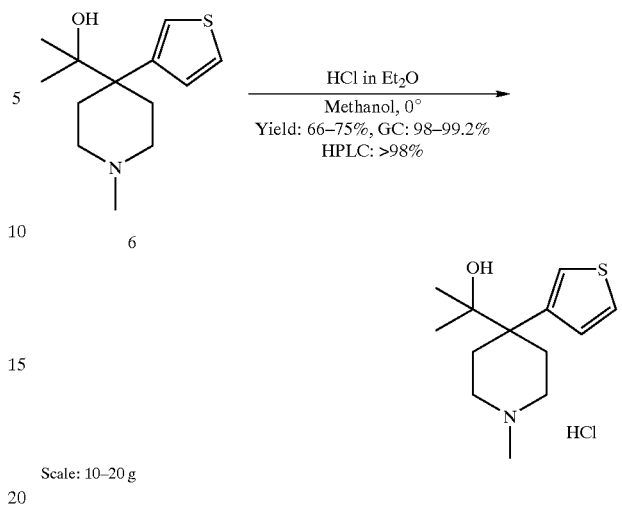

Example 12

Synthesis of the Tertiary Carbinol (6)

Ketone 5 was treated with 2 equivalents of methyllithium in THF at −78° C. Some polar additives were added to promote further conversion of ketone 5 to obtain the tertiary carbinol 6.

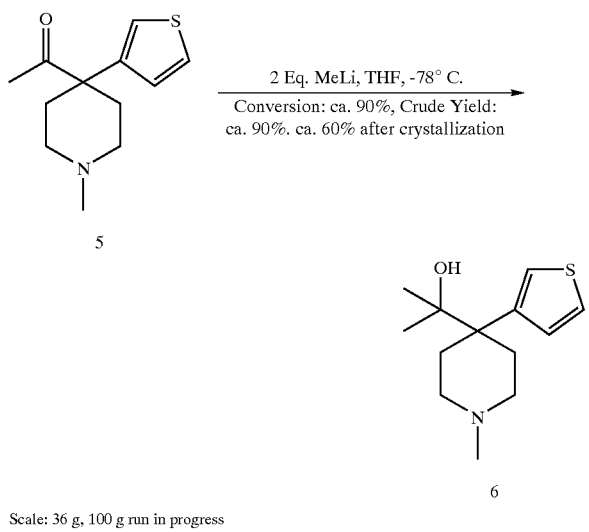

Example 13

Formation of the Hydrochloride Salt

To the tertiary carbinol 6, methanol was added and cooled to 0° C. A solution of HCl/Et$_2$O was added to obtain the hydrochloride salt. The precipitated hydrochloride salt was filtered from the suspension to obtain the salt in isolated form.

VI. Biological Methods

In neuropathic pain, it is believed that C-fiber nociceptors acquire two abnormal properties: spontaneous activity and alpha-adrenergic sensitivity. These abnormalities in nociceptor function are thought to contribute to neuropathic pain. Therefore, the compounds of the present invention have a positive effect on both, with significant inhibition of serotonin and norepinephrine synaptic uptake, implicating these compounds as useful agents for the treatment of neuropathic pain.

The antinociceptive profile of an unknown agent can be usefully assessed on the post tissue (formalin) and post nerve injury (Chung) models. This recognizes that drugs which act on the acute models will typically exert a full effect on the post tissue injury model, but not vice versa and that the post nerve injury model can have a drug activity profile distinct from the other two paradigms (Yaksh 1999). In addition, the effect of these agents on the three major classes of nociceptive processing acute post tissue injury and post nerve injury can be assessed. The present studies address the dose dependent potency of compounds of the present invention on the formalin test and upon the Chung model tactile allodynia. Compounds of the present invention were compared to venlafaxine, which has been clinically evaluated for painful diabetic neuropathy and has neurochemical and physiological similarities to the present compounds.

Various animal models were studied using these models (see Table below). The compounds of the present invention, and in particular compound A showed activity for the treatment of neuropathic pain.

| Rat | Mouse | Dog | Monkey |
|---|---|---|---|
| PQW | PQW | Tooth pulp | Tail dip |
| Tail Flick* | Tail flick[Φ] | | |
| Randell-Selitto[Φ] | | | |
| Tooth pulp | | | |

*Inactive
[Φ]Weakly active

Example 14
Serotonin and Norepinephrine Reuptake Assays

Compounds of the present invention are novel centrally acting oral non-opioids by inhibiting serotonin and norepinephrine synaptic uptake in a similar ratio to amitriptyline and venlafaxine. Inhibition of serotonin and norepinephrine synaptic uptake was found in a ~2:1 Ratio (5HT:NE), with indirect enhancement of brain enkephalin and endorphin activity and secondary opioid effects. The duration of action is greater than codeine or nalbuphine, with better efficacy for the treatment of neuropathic pain than codeine, nalbuphine and ibuprofen.

Compound A and venlafaxine are potent and selective inhibitors of rat synaptosomal 5-HT and NE Reuptake

| Compound | 5-HT uptake inhibition $IC_{50}$ (nM) | NE uptake inhibition $IC_{50}$ (nM) | 5-HT/NE inhibition $IC_{50}$ (nM) |
|---|---|---|---|
| Compound A | 120 | 223 | 1.85 |
| Venlafaxine | 210 | 640 | 3.05 |

Example 15
Formalin Model

Formalin induces inflammatory stimulation of peripheral nerves that results in sensitization of CNS nociceptive transmission pathways. There are two phases of formalin-induced nociception: phase I—an acute nociceptive component; and phase II—a chronic nociceptive component characterized by hyperalgesia.

On the morning of formalin testing, a small metal band (0.5 g) was loosely placed around the right hind paw. The rat was placed in a cylindrical Plexiglas chamber for adaptation for a minimum of 30 minutes. Compound A, venlafaxine or a saline control was administered into the dorsal surface of the right hindpaw of the rat. The animal was then placed into the chamber of the automated formalin apparatus where movement of the formalin-injected paw was monitored and the number of paw flinches tallied by minute over the next sixty minutes. Upon completion of the test the animal was removed and euthanized.

In the formalin test, statistically significant effects were seen for all administered doses of compound A during phases I, II and IIA, while venlafaxine showed statistically significant effects only during phases I and IIA. No statistical significance as compared to the saline control was seen during Phase IIB for either compound A or venlafaxine (See FIGS. 3 and 4).

Example 16
Chung Model

This model for neuropathic pain was performed on rats using the surgical procedure described by Kim and Chung (1992) to induce an allodynic state. Briefly, the left L-5 and L-6 spinal nerves were isolated adjacent to the vertebral column and ligated with 6–0 silk suture distal to the dorsal root ganglion under isoflurane anesthesia. This model allows for spinal cord structural reorganization and growth of low threshold mechnoreceptor fibers from the spinal cord with synaptic connections and rewiring of the dorsal horn. This leads to spontaneous firing of invading sympathetic nerves and upregulation of receptors and voltage-dependent channels; i.e. mimics the development of allodynia (nociceptive response to a previously neutral stimulus). The rats were allowed a minimum of 7-days postoperative recovery period before testing.

To assess tactile thresholds in the Chung model, rats were placed in a clear plastic, wire mesh-bottomed cage, divided into individual compartments. Animals were allowed to acclimate and then baseline thresholds were assessed prior to drug treatment. To assess the 50% mechanical threshold for paw withdrawal, von Frey hairs were applied to the plantar mid-hindpaw, avoiding the tori (footpads). The eight von Frey hairs used are designated by [log (10*force required to bend hair, mg)] and range from 0.4–15.1 grams (#'s 3.61–5.18). Each hair was pressed perpendicularly against the paw with sufficient force to cause slight bending, and held for approximately 6–8 seconds. A positive response was noted if the paw was sharply withdrawn. Flinching immediately upon removal of the hair was also considered a positive response. Absence of a response ("–") was cause to present the next consecutive stronger stimulus; a positive response ("+") was cause to present the next weaker stimulus. Stimuli were presented successively until either six data points were collected, or the maximum or minimum stimulus was reached. If a minimum stimulus was reached and positive responses still occurred, the threshold was assigned an arbitrary minimum value of 0.25 grams; if a maximum stimulus was presented and no response occurred, a maximum threshold value of 15 grams was assigned. If a change in response occurs, either "–" to "+" or "+" to "–", causing a change in the direction of stimulus presentation from descending to ascending or vice-versa, four additional data points were collected subsequent to the change.

In the Chung model both compound A and venlafaxine showed statistically significant effects on tactile allodynia at two hours post injection in both of the doses 200 mg/kg and 100 mg/kg. This suggests that compound A has significant antihyperpathetic effects in models of nerve and tissue injury. It is shown that compound A had a reliable dose dependent effect upon both the hyperalgesia induced by the injection of formalin into the paw and the tactile allodynia arising from nerve injury. Importantly, these effects occurred at doses where the agent had no effect upon arousal or motor function.

Example 17
Antiphenylquinone Writhing (PQW) Test

The anti-phenylquinone writhing (PQW) test modified from the methods of Siegmund et al. (Proc. Soc. Exp. Biol. Med. 95: 729–731, 1957) and Blumberg et al. (Proc. Exp. Biol. Med. 118: 763–767, 1965) was used to assess the relief from the simulated symptoms of neuropathic pain in mice. Male CF1 mice (Charles River Breeding Laboratories, Wilmington, Mass.), fasted for 16–22 hours and weighing 18–23 g, were injected with randomized and coded doses of test compounds, then challenged with 1.25 mg/kg i.p. phenyl-p-benzoquinone (phenylquinone) 5 minutes prior to the specified observation time. The phenylquinone solution (0.1 mg/ml in 5% aqueous ethanol) was prepared daily and stored in foil-wrapped amber bottles to limit degradation. Mice were observed 10 minutes for the presence or absence of the characteristic abdominal constriction and stretching response beginning 30 minutes after injection of the test compound. Activity was calculated as the percentage of mice failing to respond to the phenylquinone challenge dose. Greater than 95% of the control (vehicle-treated) mice exhibited a writhing response. Median effective doses (ED50's) and 95% confidence limits were determined numerically by the methods of Thompson (Bacteriological Rev. 11: 115–145, 1947), and Litchfield and Wilcoxon (J. Pharmacol. Exp. Ther. 96: 99–113, 1949).

|  | COMPOUND A | TRAMADOL | VENLAFAXINE |
|---|---|---|---|
| ACTIVITY | Mouse PQW: $ED_{50}$ = 18 mg/kg Rat PQW: $ED_{50}$ = 7.9 mg/kg Mouse Tail-Flick: $ED_{50}$ = 117 mg/kg Rat Tail-Flick: Inactive Rat Randall-Selitto: $ED_{50}$ = 32 mg/kg | Mouse PQW: $ED_{50}$ = 7.8 mg/kg Mouse Tail-Flick: $ED_{50}$ = 31.2 Rat Hot Plate: $ED_{50}$ = 40 mg/kg | Rat PQW: $ED_{50}$ = 39.2 mg/kg Rat Tail-Flick: Inactive Rat Hot Plate: Inactive |

Randell-Selitto/Tail Flick/Tail Dip/Tooth Pulp

Example 18
Toxicity Assay

In one embodiment of the invention, the therapeutic index for a 70 kg human was approximately 175 mg/dose (2.5 mg/kg in dog) to 2,100 mg/dose (30 mg/kg in rat).

| In Vitro Bacterial Mutagenicity: Modified Ames Test | Not mutagenic |
|---|---|
| Fourteen-day Oral Dose Range Finding Study in Rats | NOEL < 30 mg/kg (exophthalamos) MTD > 100, <300 mg/kg (decreased BW) NOAEL = 100 mg/kg |
| Five-day Oral Dose Escalation in Beagle Dogs (modified dose-range finding study) | NOEL < 2.5 mg/kg (mydriasis) MTD < 20 mg/kg (decreased BW) |

Example 19
Safety Pharmacology

| Safety Pharmacology with Compound A | | | | |
|---|---|---|---|---|
| Species | Route | Effect | Multiple of effective dose (mg/kg) | Other |
| mouse | po/iv | mydriasis | 1 X | LD = 900 mg/kg-po |
|  |  | inhibition of GI motility | 1 X |  |
|  |  | cross-tolerance to morphine | 1–50 X |  |
| dog | po | emesis/ anorexia BW loss | 1–10 X |  |
|  |  | respiratory acidosis | 10 X | $MTD^1$ = 20 mg/kg |
|  | iv-pentobarb | hypotension/ decreased cardiac contractility anemia | 10 X |  |
| rat | po | respiratory acidosis exophthalmia | 1–50 X | LD = 400 mg/kg-po LD = 270 mg/kg-sc |
|  |  | anorexia non-opioid physical dep | 10,100,300 |  |
| Monkey | iv/sc | respiratory depression Chronic dosing: | 16/32 | MTD2 = 16–32 mg/kg |
|  |  | 0.4 = retching at 7 days |  | LD = 1.6–32 mg/kg |
|  |  | 1.6 = death at 11 days 1.6 = death at 20 days non-opioid physical dep |  |  |

Example 20
Abuse Assay

Cynomologous monkeys are trained to self-administer drugs by pressing on a lever a certain number of times. The number of times an animal will press the lever before extinquishing in an attempt to self-administer drug is calculated as their fixed ratio (FR). For example, cynomologous monkeys that are trained to self-administer codeine will press the lever 300 times (FR 300) and or 10,000 times (FR 10,000) to obtain a dose of codeine. Cynomologous monkeys were trained to self-administer the compounds of the present invention. Response for compound A was achieved in one out of four monkeys. Following involuntary injections of compound A, two out of four monkeys responded with FR3 and FR10.

This invention has been described with reference to its preferred embodiments. Variations and modifications of the invention, will be obvious to those skilled in the art from the foregoing detailed description of the invention.

We claim:

1. A method for the treatment of neuropathic pain in a patient, comprising administering an effective amount of a compound of the formula:

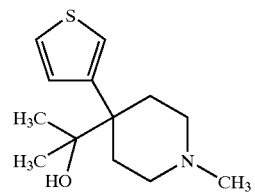

or a pharmaceutically acceptable salt or prodrug thereof.

2. The method of claim 1, wherein the compound is in the form of a dosage unit.

3. The method of claim 2, wherein the patient is a human.

4. The method of claim 2, wherein the dosage is 50–1000 mg.

5. The method of claim 2, wherein the dosage unit is an immediate release tablet, controlled release tablet, capsule, oral solution, oral suspension, pill, gel, or cream.

6. The method of claim 1, wherein the compound is suitable for oral delivery.

7. The method of claim 1, wherein the compound is suitable for parental delivery.

8. The method of claim 1, wherein the compound is suitable for intravenous delivery or intranasal delivery.

9. The method of claim 1, wherein the compound is suitable for transdermal delivery.

10. The method of claim 1, wherein the peak is suitable for rectal suppository delivery or transmucosal delivery.

11. The method of claim 1, wherein the neuropathic pain is caused by a disorder selected from carpal tunnel syndrome, cervical or lumbar radiculopathy, complex regional pain syndrome, spinal cord injury, or stump pain.

12. The method of claim 1, wherein the neuropathic pain is caused by a disorder selected from metabolic or toxic diseases.

13. The method of claim 1, wherein the neuropathic pain is caused by endocrinologic disorders.

14. The method as in claim 13, wherein the endocrinologic disorder is selected from diabetes mellitus, diabetic neuropathy, amyloidosis, or amyloid polyneuropathy.

15. The method as in claim 1, wherein the neuropathic pain is caused by a malignant tumor, Eosinophilia-myalgia syndrome, monoclonal gammopathy, mulitple sclerosis, stoke, postherpetic neuralgia, neuropathy with monoclonal protein, vasculitic neuropathy, neuropathy associated with Guillain-Barré syndrome, neuropathy associated with Fabry's disease, entrapment due to anatomic abnormality, trigeminal, CNS neuralgia, malignancy, inflammatory condition, autoimmune disorder, idiopathic distal small-fiber neuropathy, toxin, drug, dietary or absorption abnormality, immuno-globulinemia, hereditary abnormality, mastectomy, or amputation.

16. The method of claim 1, wherein the neuropathic pain is caused by a viral infection.

17. The method of claim 16, wherein the viral infection is HIV infection or herpes.

18. The method as in claim 15, wherein said autoimmune disorder is selected from the group consisting of demyelinating inflammatory disorders, rheumatoid arthritis, systemic lupus erythematosus, or Sjögren's syndrome.

19. The method as in claim 15, wherein toxin or drug is selected from the group consisting of arsenic, lead, mercury, thallium, alcohol, vincrisitne, cisplatinum, or dideoxynucleoside.

20. The method of claim 1, wherein the compound inhibits uptake of serotonin, norepinephrine, or dopamine.

21. The method of claim 1, wherein the compound inhibits ectopic activity.

22. The method of claim 1, wherein the compound inhibits ectopic discharge in the peripheral nervous system pathways.

23. The method of claim 1, wherein the compound inhibits ectopic discharge in the dorsal-root-ganglion cells of damaged afferent axons.

24. The method of claim 1, wherein the treatment is a maintenance treatment to prevent the reoccurrence of neuropathic pain.

25. A method for the treatment of neuropathic pain in a patient, comprising administering an effective amount of a compound of the formula:

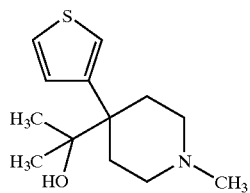

or a pharmaceutically acceptable salt or prodrug thereof, in combination or alternation with one or more other agents that are useful for the treatment of conventional or neuropathic pain.

26. A method for the treatment of neuropathic pain in a patient, comprising administering an effective amount of a compound of the formula:

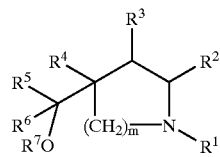

or its pharmaceutically acceptable salt or prodrug thereof, wherein:

m is 1, 2 or 3;

$R^1$ is $CH_3$, $C_2H_5$, n—$C_3H_7$ or allyl;

$R^2$ and $R^3$ independently are H or alkyl of 1–4 carbon atoms; or $R^1$ and $R^2$ taken together is a branched or unbranched alkylene bridge wherein the bridge is of 3 or 4 carbon atoms; or $R^2$ and $R^3$ taken together is a branched or unbranched alkylene bridge wherein the bridge is of 3 to 6 carbon atoms;

$R^4$ is:

(a) phenyl or

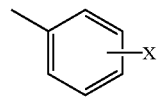

wherein X is independently one or two substituents, selected from F, Cl, Br, perfluoroalkyl, alkyl, alkyl- or dialkylamino, alkylthio, alkoxy or phenoxy, said alkyl in the alkyl-containing groups being of 1 to 12 carbon atoms;

(b) 2-, 3-, or 4-biphenyl or 2-, 3-, or 4-biphenyl where either or both aromatic groups are substituted with 1 or 2 substituents, the same or different, selected from F, Cl, alkyl, perfluoroalkyl, alkoxy, aryloxy, alkylthio, perfluoroalkoxy, arylthio, perfluoroalkylthio and dialkylamino, said alkyl and alkoxy groups being of 1–12 carbon atoms and said aryl groups being of 6–12 carbon atoms;

(c) 1- or 2-naphthyl optionally having one or two X substituents as defined in (a) above;

(d) 2-, 3-, or 4-pyridyl, or 2- or 3-pyrrolyl optionally substituted with one to three alkyl groups of 1–4 carbon atoms;

(e) 2- or 3-thienyl optionally substituted with one substituent selected from Cl, Br, or alkyl of 1–4 carbon atoms; or (f) 2- or 3-benzothienyl or benzofuryl optionally substituted on the aromatic ring with Cl, Br, or $CF_3$;

$R^5$ is alkyl of 1–4 carbon atoms, or is taken together with $R^6$ to form a branched or unbranched alkylene bridge of 3–11 carbon atoms;

$R^6$ is H, alkyl of 1–4 carbon atoms, or is taken together with $R^5$ to form a branched or unbranched alkylene bridge of 3–11 carbon atoms; and $R^7$ is H, alkyl of 1–4 carbon atoms, alkanoyl of 1–4 carbon atoms, or —$CH_2$phenyl; or a pharmaceutically salt or N-oxide thereof, provided that when (i) $R^1$, $R^5$ and $R^6$ are methyl, and $R^2$ and $R^3$ are H, then $R^4$ is not 3,4—$F_2C_6H_3$, 3,4—$Cl_2C_6H_3$, p-t-butylphenyl, 2,3-$(MeO)_2C_6H_3$, 2,5-$(MeO)_2C_6H_3$, or 3-pyridyl;

(ii) $R^1$, $R^5$ and $R^6$ are methyl or $R^5$ and $R^6$ are taken together as —(CH$_2$)$_6$— and —(CH$_2$)$_7$—, then $R^4$ not 3-(MeO)C$_6$H$_4$.

27. A method for the treatment of neuropathic pain in a patient, comprising administering an effective amount of a compound of the formula:

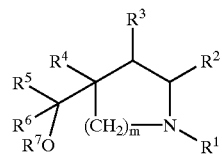

or a pharmaceutically acceptable salt or prodrug thereof, wherein:

when m is 2;

$R^1$ is CH$_3$, C$_2$H$_5$, n—C$_3$H$_7$ or allyl;

$R^2$ and $R^3$ independently are H or alkyl of 1–4 carbon atoms; or $R^1$ and $R^2$ taken together is a branched or unbranched alkylene bridge wherein the bridge is of 3 or 4 carbon atoms;

or $R^2$ and $R^3$ taken together is a branched or unbranched alkylene bridge wherein the bridge is of 3 to 6 carbon atoms;

$R^4$ is:

(a)

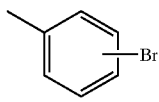

(b) 1-naphthyl optionally substituted with one or two substituents, the same or different, selected from F, Cl, Br; perfluoroalkyl, alkylthio, alkoxy, phenoxy, alkyl, alkyl- or dialkylamino, said alkyl in the alkyl-containing groups being 1–12 carbon atoms.

(c) 3-pyrrolyl optionally substituted with one to three alkyl groups of 1–4 carbon atoms, (d) 2-, or 3-thienyl optionally substituted with Cl, Br, or alkyl of 1–4 carbon atoms, provided when 2-thienyl is substituted with alkyl it is other than the 5-position, or (e) 2-, or 3-benzothienyl or benzofuryl optionally substituted on the aromatic ring with Cl, Br or CF$_3$;

$R^5$ independently is alkyl of 1–4 carbon atoms or when taken together with $R^6$ is a branched or unbranched alkylene bridge of 3–11 carbon atoms;

$R^6$ independently is alkyl of 1–4 carbon atoms, or when taken together with $R^5$ is a branched or unbranched alkylene bridge of 3–11 carbon atoms;

$R^7$ is H, alkyl of 1–4 carbon atoms, alkanoyl, or —CH$_2$phenyl.

28. A method for the treatment of neuropathic pain in a patient, comprising administering an effective amount of a compound of the formula:

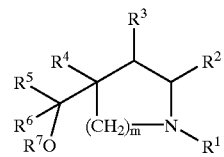

or a pharmaceutically acceptable salt or prodrug thereof, wherein:

m is 1 or 3;

$R^1$ independently is CH$_3$, C$_2$H$_5$, n—C$_3$H$_7$, or allyl;

$R^2$ and $R^3$ independently are H or alkyl of 1–4 carbon atoms; or $R^1$ and $R^2$ taken together is a branched or unbranched alkylene bridge wherein the bridge is of 3 or 4 carbon atoms;

or $R^2$ and $R^3$ taken together is a branched or unbranched alkylene bridge where the bridge is of 3 to 6 carbon atoms;

$R^4$ is:

(a) phenyl or

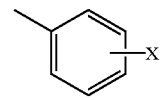

where X is one or two substituents the same or different selected from F, Cl, Br, perfluoroalkyl, alkyl, alkyl- or dialkylamino, alkylthio, alkoxy or phenoxy, said alkyl in the alkyl-containing groups being of 1 to 12 carbon atoms;

(b) 2-, 3-, or 4-biphenyl where either or both aromatic groups are substituted with 1 or 2 substituents, the same or different selected from F, Cl, alkyl, perfluoroalkyl, alkoxy, aryloxy, alkylthio, arylthio, perfluoroalkoxy, perfluoroalkylthio and dialkylamine, amino, said alkyl and alkoxy groups being of 1–12 carbon atoms and said aryl groups being of 6–12 carbon atoms;

(c) 1- or 2-naphthyl optionally having one or two X substituents as defined in (a) above;

(d) 2-, 3-, or 4-pyridyl, or 2-, or 3-pyrrolyl optionally substituted with one to three alkyl groups of 1–4 carbon atoms;

(e) 2- or 3-thienyl optionally substituted with one substituent selected from Cl, Br, or alkyl of 1–4 carbon atoms; or (f) 2- or 3-benzothienyl or benzofuryl optionally substituted on the aromatic ring with Cl, Br, or CF$_3$;

$R^5$ independently is alkyl of 1–4 carbon atoms, or when taken together with $R^6$ is a branched or unbranched alkylene bridge of 3–11 carbon atoms;

$R^6$ independently is H, alkyl of 1–4 carbon atoms, or when taken together with $R^5$ is a branched or unbranched alkylene bridge of 3–11 carbon atoms;

$R^7$ is H, alkyl of 1–4 carbon atoms, alkanoyl, or —CH$_2$phenyl; or a pharmaceutically suitable salt or N-oxide thereof.

29. A method for the treatment of neuropathic pain in a patient, comprising administering an effective amount of a compound of the formula:

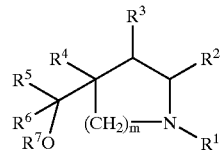

or a pharmaceutically acceptable salt or prodrug thereof, wherein:

m is 2;

$R^6$ is H;

$R^1$ independently is $CH_3$, $C_2H_5$, n—$C_3H_7$, or allyl;

$R^2$ and $R^3$ independently are H or alkyl of 1–4 carbon atoms; or $R^1$ and $R^2$ taken together is a branched or unbranched alkylene bridge wherein the bridge is of 3 or 4 carbon atoms;

or $R^2$ and $R^3$ taken together is a branched or unbranched alkylene bridge where the bridge is of 3 to 6 carbon atoms;

$R^4$ is:

(a) phenyl or

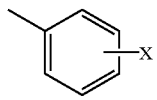

where X is one or two substituents the same or different selected from F, Cl, Br, perfluoroalkyl, alkyl, alkyl- or dialkylamino, alkylthio, alkoxy or phenoxy, said alkyl in the alkyl-containing groups being of 1 to 12 carbon atoms;

(b) 2-, 3-, or 4-biphenyl where either or both aromatic groups are substituted with 1 or 2 substituents, the same or different selected from F, Cl, alkyl, perfluoroalkyl, alkoxy, aryloxy, alkylthio, arylthio, perfluoroalkoxy, perfluoroalkylthio and dialkylamine, amino, said alkyl and alkoxy groups being of 1–12 carbon atoms and said aryl groups being of 6–12 carbon atoms;

(c) 1- or 2-naphthyl optionally having one or two X substituents as defined in (a) above;

(d) 2-, 3-, or 4-pyridyl, or 2-, or 3-pyrrolyl optionally substituted with one to three alkyl groups of 1–4 carbon atoms;

(e) 2- or 3-thienyl optionally substituted with one substituent selected from Cl, Br, or alkyl of 1–4 carbon atoms; or (f) 2- or 3-benzothienyl or benzofuryl optionally substituted on the aromatic ring with Cl, Br, or $CE_3$;

$R^5$ independently is alkyl of 1–4 carbon atoms;

$R^7$ is H, alkyl of 1–4 carbon atoms, alkanoyl, or —$CH_2$phenyl; or a pharmaceutically suitable salt or N-oxide thereof.

30. A method for the treatment of neuropathic pain in a patient, comprising administering an effective amount of a compound of the formula:

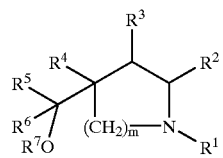

or a pharmaceutically acceptable salt or prodrug thereof, wherein:

m is 2;

$R^6$ is H;

$R^1$ is methyl;

$R^2$ and $R^3$ independently are H or alkyl of 1–4 carbon atoms; or $R^2$ and $R^3$ taken together is a branched or unbranched alkylene bridge where the bridge is of 3 to 6 carbon atoms;

$R^4$ is:

(a)

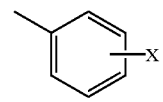

where X is one or two substituents the same or different selected from F, Cl, Br, perfluoroalkyl, alkyl, alkyl- or dialkylamino, alkylthio, alkoxy or phenoxy, said alkyl in the alkyl-containing groups being of 1 to 12 carbon atoms;

(b) 2-, 3-, or 4-biphenyl where either or both aromatic groups are substituted with 1 or 2 substituents, the same or different selected from F, Cl, alkyl, perfluoroalkyl, alkoxy, aryloxy, alkylthio, arylthio, perfluoroalkoxy, perfluoroalkylthio and dialkylamine, amino, said alkyl and alkoxy groups being of 1–12 carbon atoms and said aryl groups being of 6–12 carbon atoms;

(c) 1- or 2-naphthyl optionally having one or two X substituents as defined in (a) above;

(d) 2-, 3-, or 4-pyridyl, or 2-, or 3-pyrrolyl optionally substituted with one to three alkyl groups of 1–4 carbon atoms;

(e) 2- or 3-thienyl optionally substituted with one substituent selected from Cl, Br, or alkyl of 1–4 carbon atoms; or (f) 2- or 3-benzothienyl or benzofuryl optionally substituted on the aromatic ring with Cl, Br, or $CF_3$;

$R^5$ independently is alkyl of 1–4 carbon atoms;

$R^7$ is H, alkyl of 1–4 carbon atoms, alkanoyl, or —$CH_2$phenyl; or a pharmaceutically suitable salt or N-oxide thereof.

31. A method for the treatment of neuropathic pain in a patient, comprising administering an effective amount of a compound of the formula:

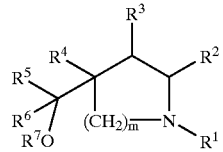

or a pharmaceutically acceptable salt or prodrug thereof, wherein:

m is 2;
(a) $R^1$ is $CH_3$;
(b) $R^2$ and $R^3$ are H;
(c) $R^4$ is 2- or 3-thienyl,

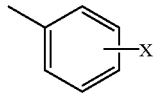

where X is Cl, Br, F, $CF_3$;
(d) $R^5$ is $CH_3$;
(e) $R^6$ is H or $CH_3$; and
(f) $R^7$ is H.

32. A method for the treatment of neuropathic pain in a patient, comprising administering an effective amount of a compound of the formula:

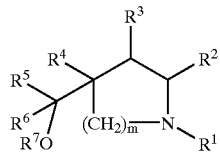

or a pharmaceutically acceptable salt or prodrug thereof, wherein:

m is 1 or 3;
(a) $R^1$ is $CH_3$;
(b) $R^2$, $R^3$ and $R^7$ are H;
(c) $R^4$ is

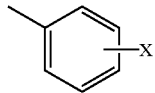

where X is Cl, Br, F or $CF_3$; or
(d) $R^5$ is $CH_3$; and
(e) $R^6$ is H or $CH_3$.

33. The method of claim 26, wherein the compound is selected from the group consisting of:
   (a) 4-(3'-Thienyl)-α,α,1-trimethyl-4-piperidinemethanol;
   (b) 4-(3'-Chlorophenyl)-α,1-dimethylpiperidinemethanol;
   (c) 4-(3'-Chlorophenyl)-α,α,1-trimethyl-4-piperidinemethanol;
   (d) 4-(3'-Bromophenyl)-α,1-dimethylpiperidinemethanol;
   (e) 4-(3'-Bromophenyl)-α,α,1-trimethyl-4-piperidinemethanol;
   (f) 4-(2-Thienyl)-α,1-dimethylpiperidinemethanol;
   (g) 4-(3-Thienyl)-α,1-dimethylpiperidinemethanol;
   (h) 4-(3'-Chlorophenyl)-α,1-dimethyl-2,3,4,5,6,7-hexahydro-1H-azepine-1-methanol;
   (i) 3-(3'-Chlorophenyl)-α,α,1-trimethyl-3-pyrrolidinemethanol;
   (j) 4(4'-Trifluoromethylphenyl)-α,1-dimethylpiperidinemethanol;

or a pharmaceutically suitable salt thereof.

34. A method for the treatment neuropathic pain in a patient, comprising administering an effective amount of a compound of the formula:

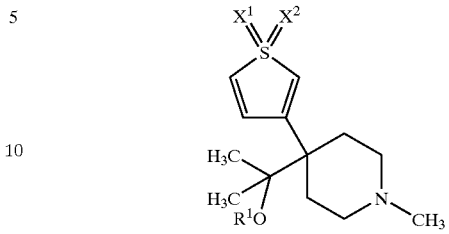

or its pharmaceutically acceptable salt or prodrug thereof, wherein:

$X^1$ and $X^2$ are independently O or $NR^2$; and
$R^1$ is H, alkyl, lower alkyl (such as a $C_1$ to $C_6$ optionally substituted branched or straight-chained alkyl); alkenyl, alkynyl, acyl, —C(O)$R^5$, —C(O)$NR^5R^6$, —C(O)$OR^5$, —C(O)$SR^5$, —C(S)$R^5$, —C(S)$NR^5R^6$, —C(S)$OR^5$, —C(S)$SR^5$, —C($NR^7$)$R^5$, —C($NR^7$)$NR^5R^6$, —C($NR^7$)$OR^5$, —C($NR^7$)$SR^5$ or phosphate; and $R^2$, $R^5$, $R^6$ and $R^7$ are independently H or alkyl.

35. The method of claim 26, wherein the compound administered does not show significant activity at mu, kappa, delta, or sigma receptor sites in the brain.

36. The method of claim 26, wherein the compound administered lacks addictive or respiratory depressant properties.

37. The method of claim 26, wherein the compound administered does not inhibit prostaglandin synthesase activity.

38. The method of claim 26, wherein the compound administered does not exhibit an anti-inflammatory effect in vivo.

39. The method of claim 26, wherein the compound administered inhibits uptake of serotonin, norepinephrine, or dopamine.

40. The method of claim 26, wherein the compound administered does not exhibit anticholinergic side effects, sedation, or motor impairment.

41. The method of claim 26, wherein the treatment is a maintenance treatment to prevent the reoccurrence of neuropathic pain.

42. The method of claim 25, wherein the treatment is a maintenance treatment to prevent the reoccurrence of neuropathic pain.

43. The method of claim 26, wherein the compound is in the form of a dosage unit.

44. The method of claim 26, wherein the patient is a human.

45. The method of claim 43, wherein the dosage is 50–1000 mg.

46. The method of claim 43, wherein the dosage unit is an immediate release tablet, controlled release tablet, capsule, oral solution, oral suspension, or pill.

47. The method of claim 26, wherein the compound is suitable for orally delivery.

48. The method of claim 26, wherein the compound is suitable for parental delivery.

49. The method of claim 26, wherein the compound is suitable for intravenous delivery, transdermal delivery, intranasal delivery, rectal suppository delivery, or transmucosal delivery.

50. The method of claim 26, wherein the neuropathic pain is caused by a disorder selected from carpal tunnel syndrome, cervical or lumbar radiculopathy, complex regional pain syndrome, spinal cord injury, or stump pain.

51. The method of claim 26, wherein the neuropathic pain is caused by a disorder selected from metabolic or toxic diseases.

52. The method of claim 26, wherein the neuropathic pain is caused by endocrinologic disorder.

53. The method of claim 52, wherein the endocrinologic disorder is selected from diabetes mellitus, diabetic neuropathy, amyloidosis, or amyloid polyneuropathy.

54. The method of claim 26, wherein the neuropathic pain is caused by a malignant tumor, Eosinophilia-myalgia syndrome, monoclonal gammopathy, mulitiple sclerosis stroke, postherpetic neuralgia, neuropathy with monoclonal protein, vasculitic neuropathy, neuropathy associated with Guillain-Barré syndrome, neuropathy associated with Fabry's disease, entrapment due to anatomic abnormality, trigeminal, CNS neuralgia, malignancy, inflammatory condition, autoimmune disorder, idiopathic distal small-fiber neuropathy, toxin, drug, dietary or absorption abnormality, immuno-globulinemia, hereditary abnormality, mastectomy, or amputation.

55. The method of claim 26, wherein the neuropathic pain is caused by a viral infection.

56. The method of claim 54, wherein the viral infection is HIV infection or herpes.

57. The method of claim 54, wherein said autoimmune disorder is selected from a group consisting of demyelinating inflammatory disorder, rheumatoid arthritis, systemic lupus erythematosus, or Sjögren's syndrome.

58. The method of claim 54, wherein toxin or drug is selected from the group consisting of arsenic, lead, mercury, thallium, alcohol, vincrisitne, cisplatinum, or dideoxy-nucleoside.

* * * * *

UNITED STATES PATENT AND TRADEMARK OFFICE
CERTIFICATE OF CORRECTION

PATENT NO. : 6,825,217 B2
DATED : November 30, 2004
INVENTOR(S) : Carliss et al.

It is certified that error appears in the above-identified patent and that said Letters Patent is hereby corrected as shown below:

Column 43,
Line 14, change "stoke" to -- stroke --.

Signed and Sealed this

Thirty-first Day of January, 2006

JON W. DUDAS
*Director of the United States Patent and Trademark Office*